United States Patent
Shelton, IV et al.

(10) Patent No.: US 9,867,608 B1
(45) Date of Patent: Jan. 16, 2018

(54) SUTURING INSTRUMENT WITH CIRCULAR NEEDLE MOTION

(71) Applicant: Ethicon Endo-Surgery, LLC, Guaynabo, PR (US)

(72) Inventors: Frederick E. Shelton, IV, Hillsboro, OH (US); Trevor J. Barton, Cincinnati, OH (US); Charles J. Scheib, Loveland, OH (US); Andrew C. Deck, Dayton, OH (US); David T. Martin, Milford, OH (US); William J. White, West Chester, OH (US); Emily A. Schellin, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 211 days.

(21) Appl. No.: 14/740,924

(22) Filed: Jun. 16, 2015

(51) Int. Cl.
*A61B 17/04* (2006.01)

(52) U.S. Cl.
CPC ...... *A61B 17/0469* (2013.01); *A61B 17/0482* (2013.01); *A61B 2017/0498* (2013.01)

(58) Field of Classification Search
CPC .......... A61B 17/00234; A61B 17/0469; A61B 17/0482; A61B 17/062; A61B 17/0625; A61B 2017/0023; A61B 2017/00314; A61B 2017/00349; A61B 2017/0046; A61B 2017/00473; A61B 2017/0479; A61B 2017/0608
See application file for complete search history.

(56) References Cited

U.S. PATENT DOCUMENTS

| | | | | | |
|---|---|---|---|---|---|
| 4,027,608 | A | * | 6/1977 | Arbuckle | D05B 81/00 112/169 |
| 4,557,265 | A | * | 12/1985 | Andersson | A61B 17/0491 112/222 |
| 4,899,746 | A | * | 2/1990 | Brunk | A61B 17/0491 112/169 |
| 5,709,693 | A | * | 1/1998 | Taylor | A61B 17/0491 606/139 |
| 5,766,186 | A | * | 6/1998 | Faraz | A61B 17/0469 606/145 |
| 5,911,727 | A | * | 6/1999 | Taylor | A61B 17/0491 606/139 |
| 6,443,962 | B1 | * | 9/2002 | Gaber | A61B 17/0491 112/80.04 |
| 7,004,951 | B2 | * | 2/2006 | Gibbens, III | A61B 17/0482 606/144 |
| 7,338,504 | B2 | * | 3/2008 | Gibbens | A61B 17/0482 606/144 |

(Continued)

*Primary Examiner* — Ryan J Severson
(74) *Attorney, Agent, or Firm* — Frost Brown Todd LLC

(57) ABSTRACT

A surgical instrument includes a body, an input feature, an elongate shaft, and a needle applier. The needle applier is coupled to the elongate shaft, which extends distally from the body. The needle applier includes a needle, a drive assembly, and a guide assembly. The drive assembly includes a link configured to drive the needle orbitally about a rotation axis that is transverse to the longitudinal axis of the shaft in response to actuation of the input feature. The guide assembly is in communication with the input feature and the drive assembly. The guide assembly is responsive to the input feature to guide a distal portion of the link along a semi-circular path.

20 Claims, 22 Drawing Sheets

(56) References Cited

U.S. PATENT DOCUMENTS

| | | | | |
|---|---|---|---|---|
| 7,628,796 B2 * | 12/2009 | Shelton, IV | A61B 1/00087 | 606/139 |
| 7,828,812 B2 * | 11/2010 | Stokes | A61B 1/00087 | 606/139 |
| 7,833,236 B2 * | 11/2010 | Stokes | A61B 1/00087 | 606/139 |
| 7,862,572 B2 * | 1/2011 | Meade | A61B 17/0482 | 606/145 |
| 7,887,554 B2 * | 2/2011 | Stokes | A61B 1/00087 | 606/139 |
| 7,976,553 B2 * | 7/2011 | Shelton, IV | A61B 1/00087 | 606/139 |
| 8,123,764 B2 * | 2/2012 | Meade | A61B 17/0469 | 606/139 |
| 8,474,522 B2 * | 7/2013 | Lynde | E21B 21/002 | 166/99 |
| 8,500,756 B2 * | 8/2013 | Papa | A61B 1/00087 | 606/139 |
| 8,641,728 B2 * | 2/2014 | Stokes | A61B 1/00087 | 606/139 |
| 8,702,732 B2 * | 4/2014 | Woodard, Jr. | A61B 17/0469 | 606/147 |
| 8,821,519 B2 * | 9/2014 | Meade | A61B 17/0469 | 606/139 |
| 8,906,043 B2 * | 12/2014 | Woodard, Jr. | A61B 17/0469 | 606/147 |
| 9,113,861 B2 * | 8/2015 | Martin | A61B 17/062 | |
| 9,125,645 B1 * | 9/2015 | Martin | A61B 17/0469 | |
| 9,168,037 B2 * | 10/2015 | Woodard, Jr. | A61B 17/0469 | |
| 9,247,938 B2 * | 2/2016 | Martin | A61B 17/062 | |
| 9,277,916 B2 * | 3/2016 | Martin | A61B 17/0469 | |
| 9,357,998 B2 * | 6/2016 | Martin | A61B 17/0483 | |
| 9,375,212 B2 * | 6/2016 | Martin | A61B 17/0482 | |
| 9,427,226 B2 * | 8/2016 | Martin | A61B 17/0469 | |
| 9,451,946 B2 * | 9/2016 | Woodard, Jr. | A61B 17/0469 | |
| 9,474,522 B2 | 10/2016 | Deck et al. | | |
| 2003/0083674 A1 * | 5/2003 | Gibbens, III | A61B 17/0482 | 606/144 |
| 2006/0069396 A1 * | 3/2006 | Meade | A61B 17/0482 | 606/144 |
| 2006/0111732 A1 * | 5/2006 | Gibbens | A61B 17/0482 | 606/145 |
| 2006/0281970 A1 * | 12/2006 | Stokes | A61B 1/00087 | 600/104 |
| 2006/0282090 A1 * | 12/2006 | Stokes | A61B 1/00087 | 606/144 |
| 2006/0282091 A1 * | 12/2006 | Shelton, IV | A61B 1/00087 | 606/144 |
| 2006/0282092 A1 * | 12/2006 | Stokes | A61B 1/00087 | 606/144 |
| 2006/0282093 A1 * | 12/2006 | Shelton, IV | A61B 1/00087 | 606/144 |
| 2006/0282094 A1 * | 12/2006 | Stokes | A61B 1/00087 | 606/144 |
| 2006/0282095 A1 * | 12/2006 | Stokes | A61B 1/00087 | 606/144 |
| 2006/0282096 A1 * | 12/2006 | Papa | A61B 1/00087 | 606/144 |
| 2006/0282098 A1 * | 12/2006 | Shelton, IV | A61B 1/00087 | 606/144 |
| 2006/0282099 A1 * | 12/2006 | Stokes | A61B 1/00087 | 606/148 |
| 2007/0239176 A1 * | 10/2007 | Stokes | A61B 17/00234 | 606/144 |
| 2007/0239177 A1 * | 10/2007 | Stokes | A61B 17/0469 | 606/144 |
| 2008/0255590 A1 * | 10/2008 | Meade | A61B 17/0482 | 606/144 |
| 2009/0108048 A1 * | 4/2009 | Zemlok | A61B 17/07207 | 227/175.1 |
| 2009/0209980 A1 * | 8/2009 | Harris | A61B 17/0491 | 606/144 |
| 2010/0152751 A1 * | 6/2010 | Meade | A61B 17/0469 | 606/144 |
| 2011/0278344 A1 * | 11/2011 | Zemlok | A61B 17/07207 | 227/176.1 |
| 2012/0130404 A1 * | 5/2012 | Meade | A61B 17/0469 | 606/145 |
| 2012/0143223 A1 * | 6/2012 | Woodard, Jr. | A61B 17/0469 | 606/147 |
| 2012/0220989 A1 * | 8/2012 | Zemlok | A61B 17/07207 | 606/1 |
| 2012/0289975 A1 * | 11/2012 | Martin | A61B 17/062 | 606/147 |
| 2012/0290005 A1 * | 11/2012 | Martin | A61B 17/062 | 606/232 |
| 2013/0245647 A1 * | 9/2013 | Martin | A61B 17/0469 | 606/147 |
| 2013/0245648 A1 * | 9/2013 | Martin | A61B 17/0469 | 606/147 |
| 2013/0282027 A1 * | 10/2013 | Woodard, Jr. | A61B 17/0469 | 606/144 |
| 2013/0282031 A1 * | 10/2013 | Woodard, Jr. | A61B 17/062 | 606/147 |
| 2014/0171970 A1 * | 6/2014 | Martin | A61B 17/0483 | 606/144 |
| 2015/0090764 A1 * | 4/2015 | Zemlok | A61B 17/07207 | 227/176.1 |
| 2015/0127024 A1 * | 5/2015 | Berry | A61B 17/0469 | 606/145 |
| 2015/0133967 A1 * | 5/2015 | Martin | A61B 17/0482 | 606/144 |
| 2015/0142020 A1 * | 5/2015 | Woodard, Jr. | A61B 17/0469 | 606/147 |
| 2015/0327857 A1 * | 11/2015 | Zemlok | A61B 17/07207 | 227/176.1 |
| 2015/0351748 A1 * | 12/2015 | White | A61B 17/0482 | 606/145 |
| 2016/0120740 A1 * | 5/2016 | Rawls-Meehan | A61H 23/0263 | 601/49 |
| 2016/0367238 A1 * | 12/2016 | Deck | A61B 17/0469 | |
| 2016/0367243 A1 * | 12/2016 | Martin | A61B 17/0469 | |

* cited by examiner

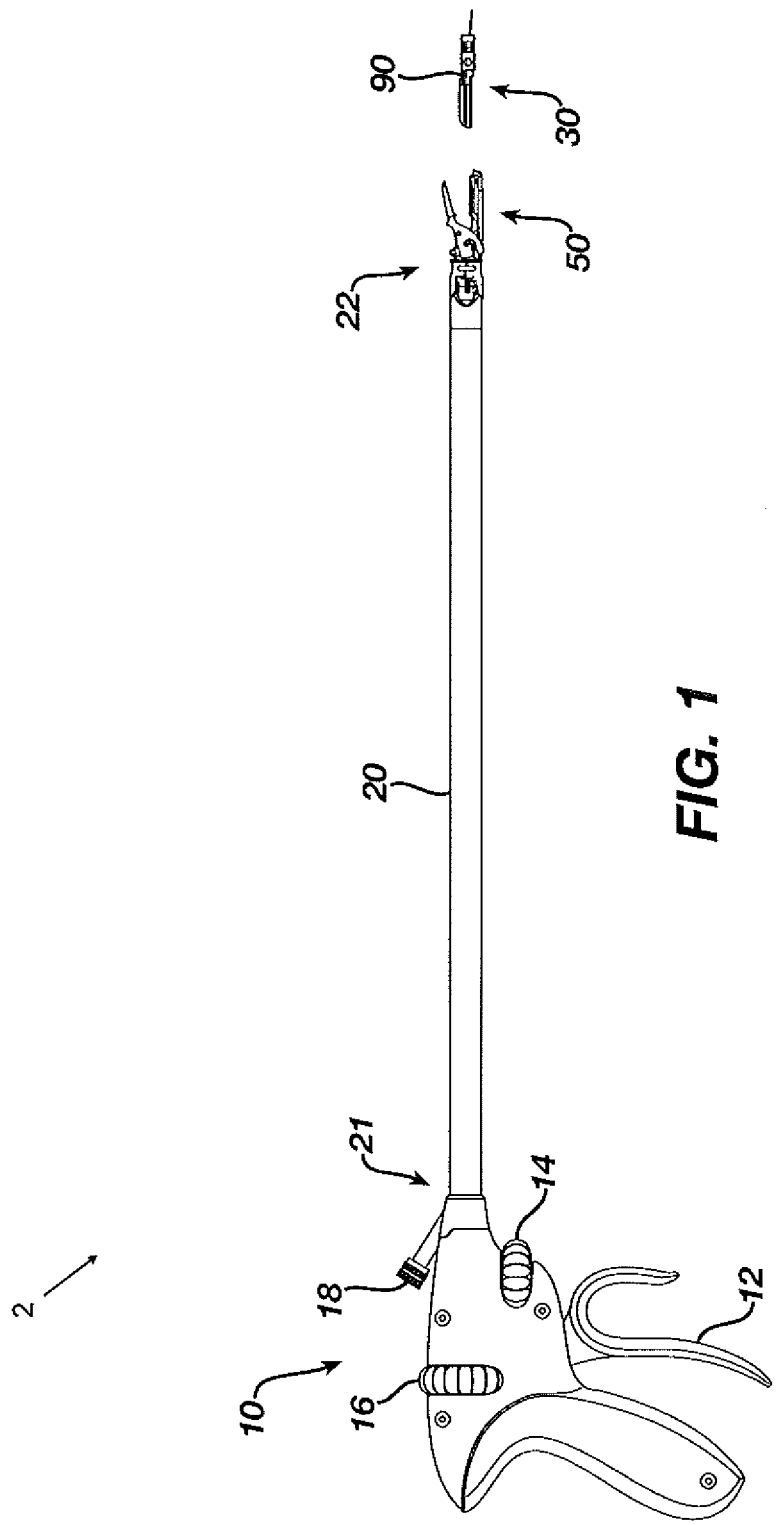

US 9,867,608 B1

SUTURING INSTRUMENT WITH CIRCULAR NEEDLE MOTION

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laparoscopic Suture Device with Asynchronous In-Line Needle Movement," published Dec. 22, 2011, now U.S. Pat. No. 9,168,037, issued Oct. 27, 2015, the disclosure of which is incorporated by reference herein; U.S. Pub. No. 2014/0171970, entitled "Circular Needle Applier with Articulating and Rotating Shaft," published Jun. 19, 2014, now U.S. Pat. No. 9,357,998, issued Jun. 7, 2016, the disclosure of which is incorporated by reference herein; and U.S. patent application Ser. No. 14/297,993, entitled "Jawed Cartridge receiving assembly for Needle Cartridge," filed Jun. 6, 2014, now U.S. Pat. No. 9,474,522, issued Oct. 25, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a side view of an exemplary surgical suturing instrument;

Figure 2A:
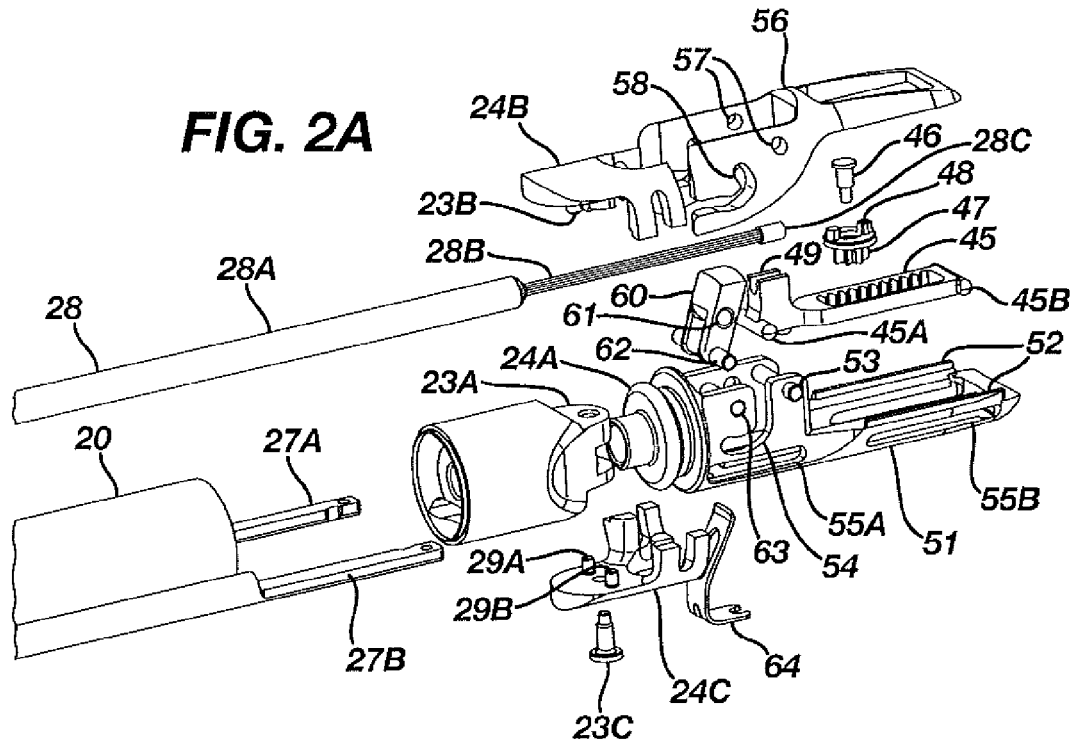
FIG. 2A depicts top perspective exploded view of a cartridge receiving assembly of the instrument of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Surgical Suturing Instrument

FIG. 1 illustrates an example of a surgical suturing instrument (2). Instrument (2) comprises a handle assembly (10), an elongate shaft (20), and a cartridge receiving assembly (50), which is operable to receive a needle applier cartridge (30). Shaft (20) has a proximal end (21), a distal end (22), and a longitudinal axis extending therebetween. Handle assembly (10) is connected to the proximal end (21) of the shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to the distal end (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first input (12), shown here as a trigger that pivots between opened and closed positions, may be used to selectively actuate needle applier cartridge (30). The trigger may be spring biased to return the trigger to its open position. A second input (14), shown here as a rotary knob, may be used to selectively articulate shaft (20). A third input (16), shown here as a rotary knob, may be used to selectively rotate needle applier cartridge (30) about shaft (20). Of course, the number, type, configuration, and operation of inputs (12, 14, 16) may vary.

Figure 2B:
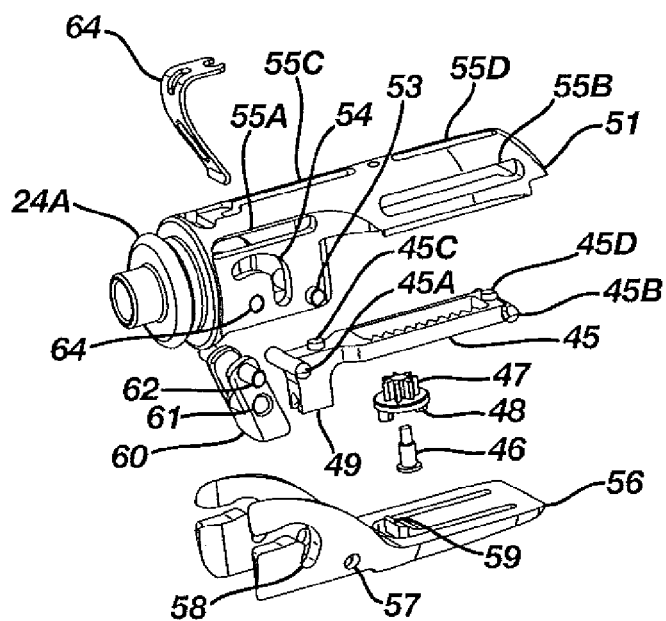
FIG. 2B depicts bottom perspective exploded view of the cartridge receiving assembly of FIG. 2A.

FIGS. 2A-2B illustrate exploded views of cartridge receiving assembly (50) of the present example. Distal end (22) of shaft (20) comprises an articulation joint (23) and a rotational bearing (24). Articulation joint (23) includes a knuckle (23A) that receives pins (23B, 23C), which are connected to bearing supports (24B, 24C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to second input (14) to opposingly push and pull rods (27A, 27B). In other words, second input (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by the pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first input (12) and to third input (16). Actuation of first input (12) will impart axial push and pull loads on drive rod (28) to longitudinally reciprocate rack (45) and thereby actuate needle applier cartridge (30). Actuation of third input (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the open configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
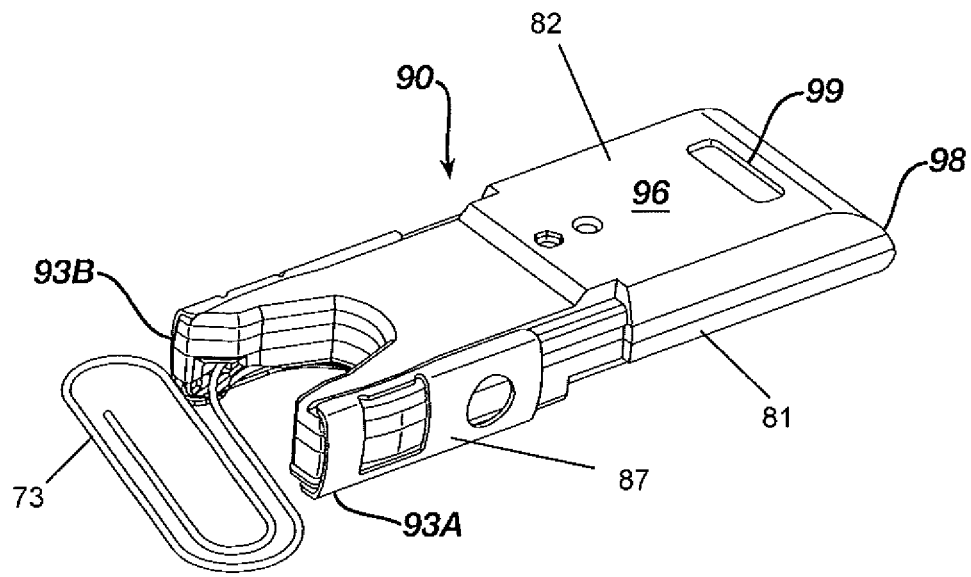
FIG. 3A depicts a top perspective view of an exemplary cartridge configured for receipt in the cartridge receiving assembly of FIG. 2A.
Figure 3B:
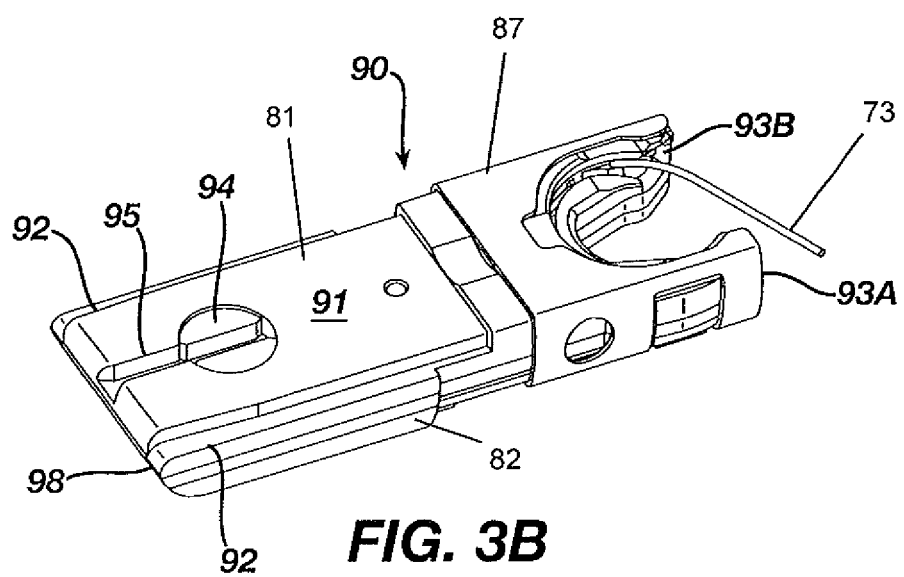
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
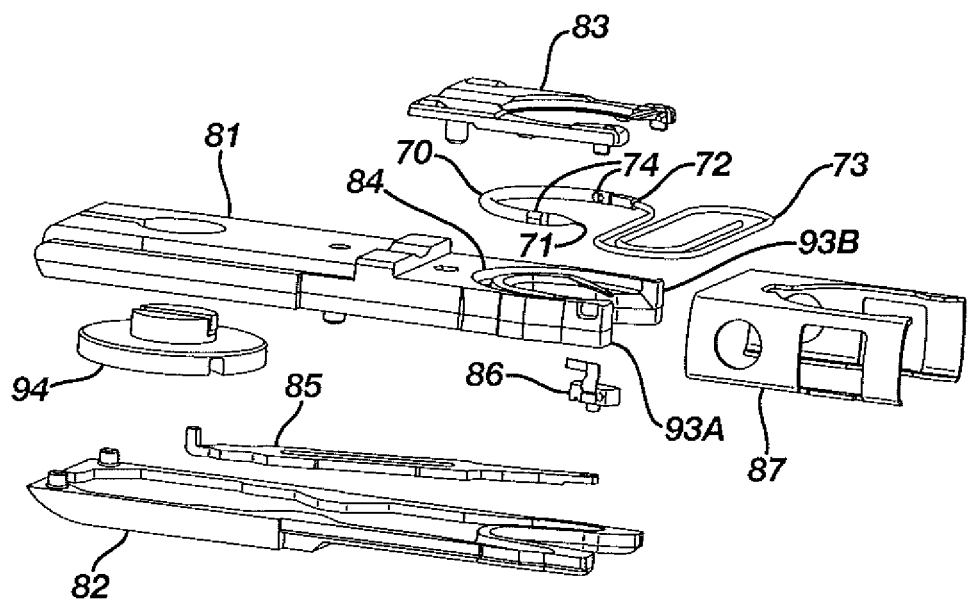
FIG. 4 depicts an exploded view of the cartridge of FIG. 3A.

As shown in FIGS. 3A-4, cartridge body (90) further comprises a lower body (81), an upper body (82), a needle (70), and a needle cover (83). Needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from the trailing end (72). Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
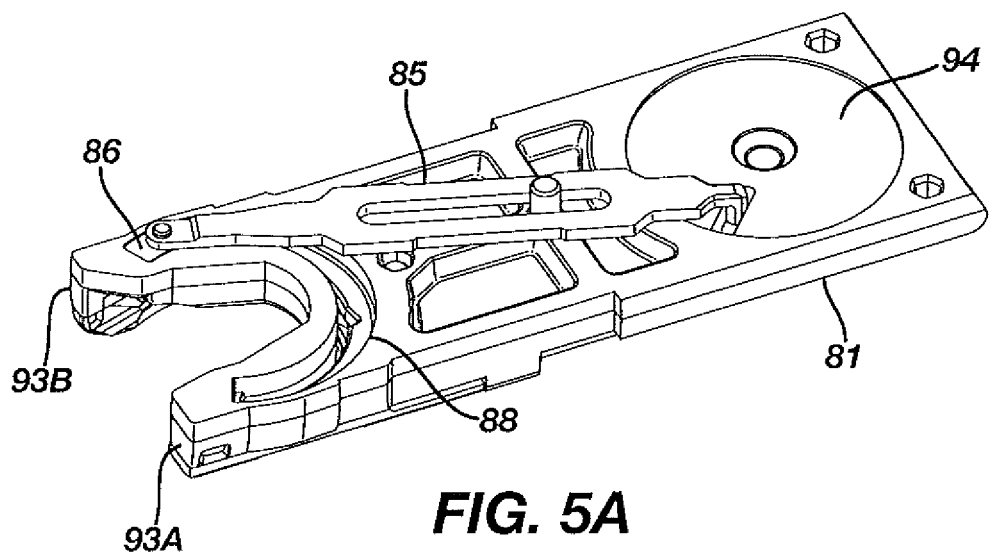
FIG. 5A depicts a perspective view of a drive assembly of the cartridge of FIG. 3A, with the drive assembly at one end of its stroke.
Figure 5B:
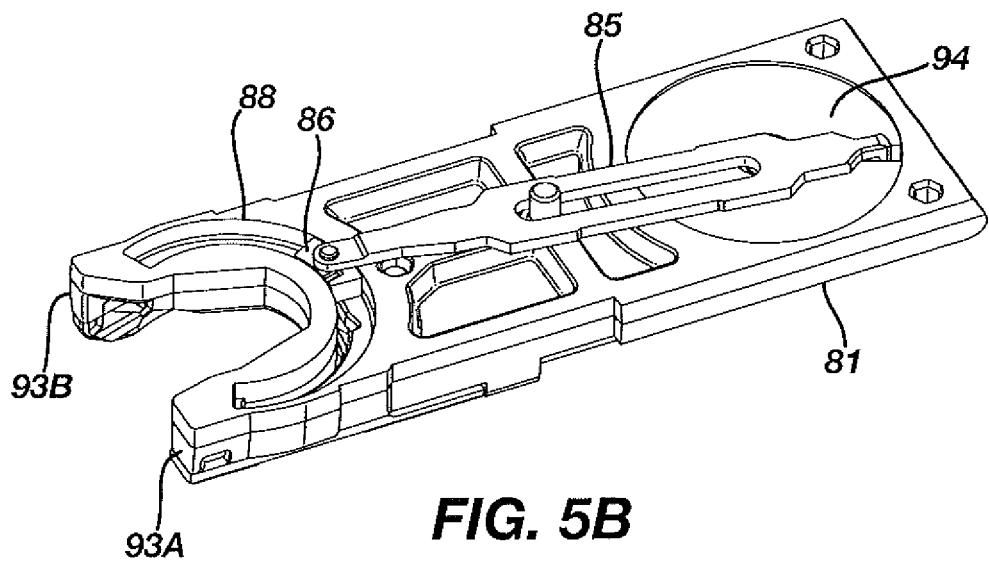
FIG. 5B depicts a perspective view of the drive assembly of FIG. 5A, with the drive assembly at mid-stroke.
Figure 5C:
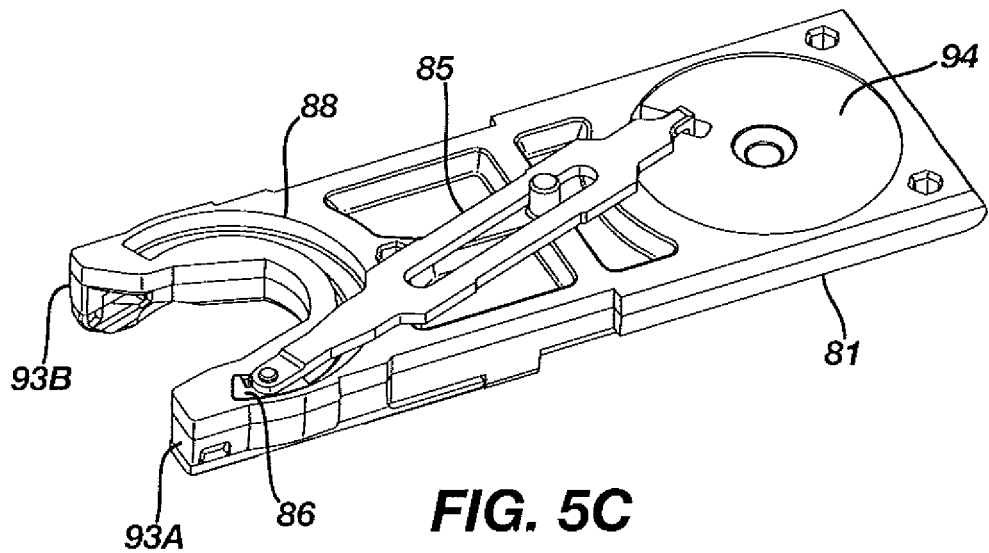
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) omitted from FIGS. 5B-5C. Needle driver (86) rides in a carrier track (88) and extends into needle track (84) to engage and drive needle (70). A link (85) connects rotary input (94) to needle driver (86). FIG. 5A shows needle driver (86) positioned at one end of its stroke in carrier track (88). As shown in FIG. 5B, counter-clockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
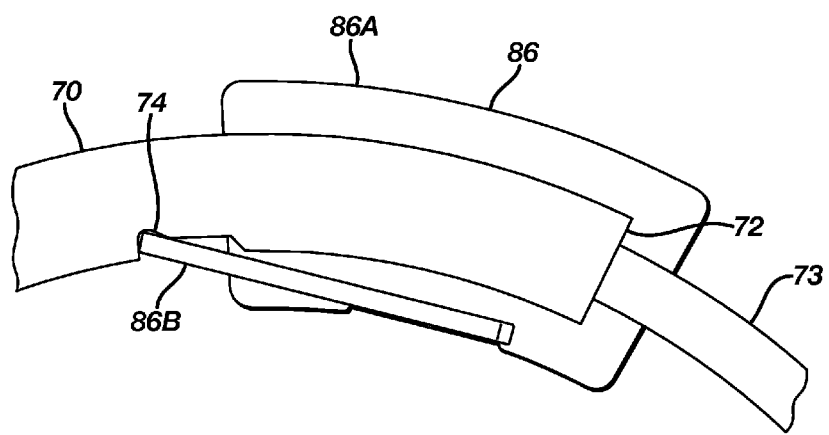
FIG. 6 depicts a partial plan view of a needle driver of the cartridge of FIG. 3A engaging a needle of the cartridge of FIG. 3A.

FIG. 6 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (75) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C, when first input (12) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (95) and entrance port (97). Tissue interposed between arms (93A, 93B) will be pierced by leading end (71) of needle (70).

When first input (12) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first input (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) will follow needle (70) and be threaded through the pierced tissue.

When first input (12) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first input (12) being actuated twice. The sequence may be repeated as needed by the surgeon to achieve the desired suturing task.

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, now U.S. Pat. No. 9,357,998, issued Jun. 7, 2016, the disclosure of which is incorporated by reference herein; U.S. patent application Ser. No. 14/297,993, entitled "Jawed Cartridge Receiving Assembly for Needle Cartridge," filed Jun. 6, 2014, now U.S. Pat. No. 9,474,522, issued Oct. 25, 2016, the disclosure of which is incorporated by reference herein; and U.S. patent application Ser. No. 14/298,038, entitled "Circular Needle Applier with Cleats," filed Jan. 30, 2015, now U.S. Pat. No. 9,375,212, issued Jun. 28, 2016, the disclosure of which is incorporated by reference herein. It should be understood that such details, explanations, examples, and alternative embodiments may be readily applied to the above-described instrument (10) and subcomponents thereof.

II. Exemplary Alternative Needle Applier Cartridges

In some instances it may be desirable to use instrument (2) in conjunction with a needle applier cartridge similar to needle applier cartridge (30) described above, but with various alternative features related to driving a needle driver like needle driver (86). For instance, in one such needle applier cartridge it may be desirable to include features configured to maintain movement of a link, similar to link (85) described above, in a relatively circular path. In other needle applier cartridges it may be desirable to provide a linear drive input as an alternative to rotary input (94) described above. Needle applier cartridges having such features may be desirable to generally improve the usability of instrument (2). For example, such features may contribute to driving the needle driver more fluidly than needle driver (86), thus making first input (12) more easily actuated by a surgeon. Additionally, certain features described below may require fewer components making the instrument less expensive and easier to clean.

Various examples are described below that incorporate the alternative forms of needle applier cartridge (30) described above. It should be understood that the examples described below are merely illustrative. Various other alternative needle applier cartridges incorporating similar features will be apparent to those of ordinary skill in the art in view of the teachings herein.

A. Exemplary Alternative Needle Applier Cartridge with Rotary Oscillating Input

Figure 7:
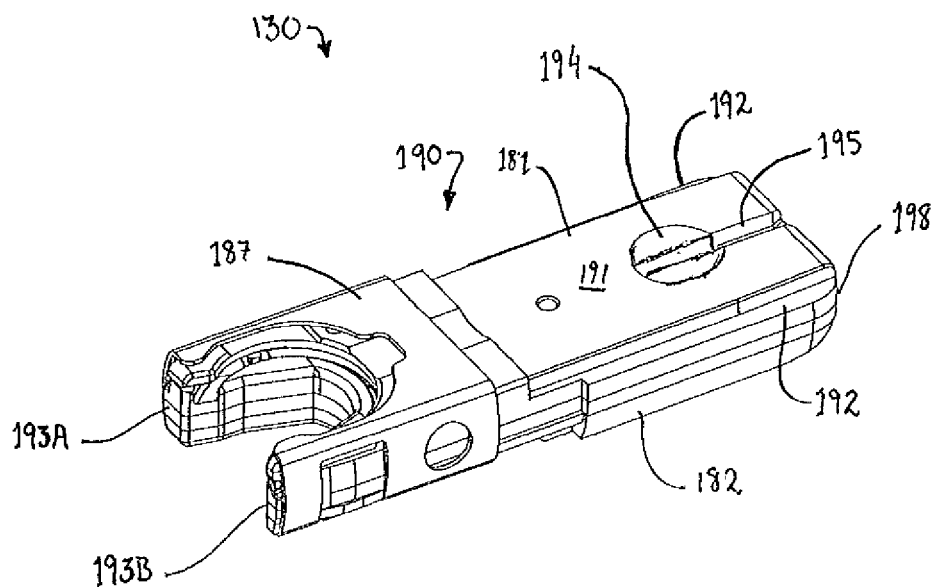
FIG. 7 depicts a perspective view of another exemplary cartridge configured for receipt in the cartridge receiving assembly of FIG. 2A.
Figure 8:
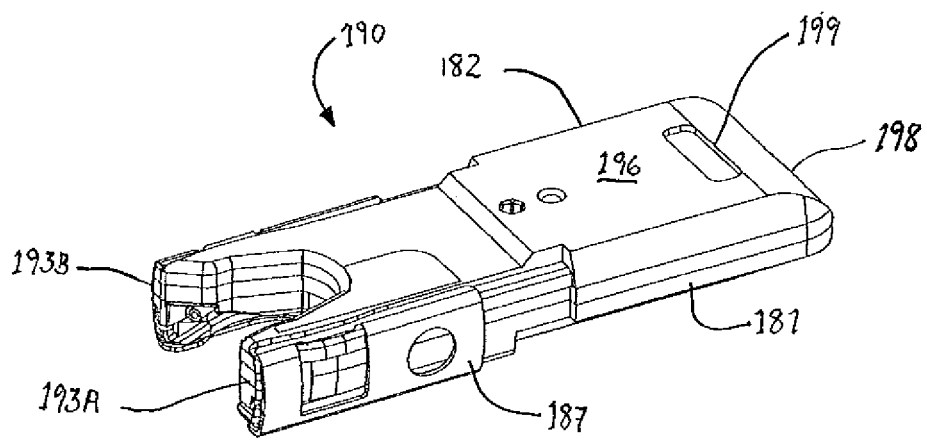
FIG. 8 depicts another perspective view of the cartridge of FIG. 7.
Figure 9:
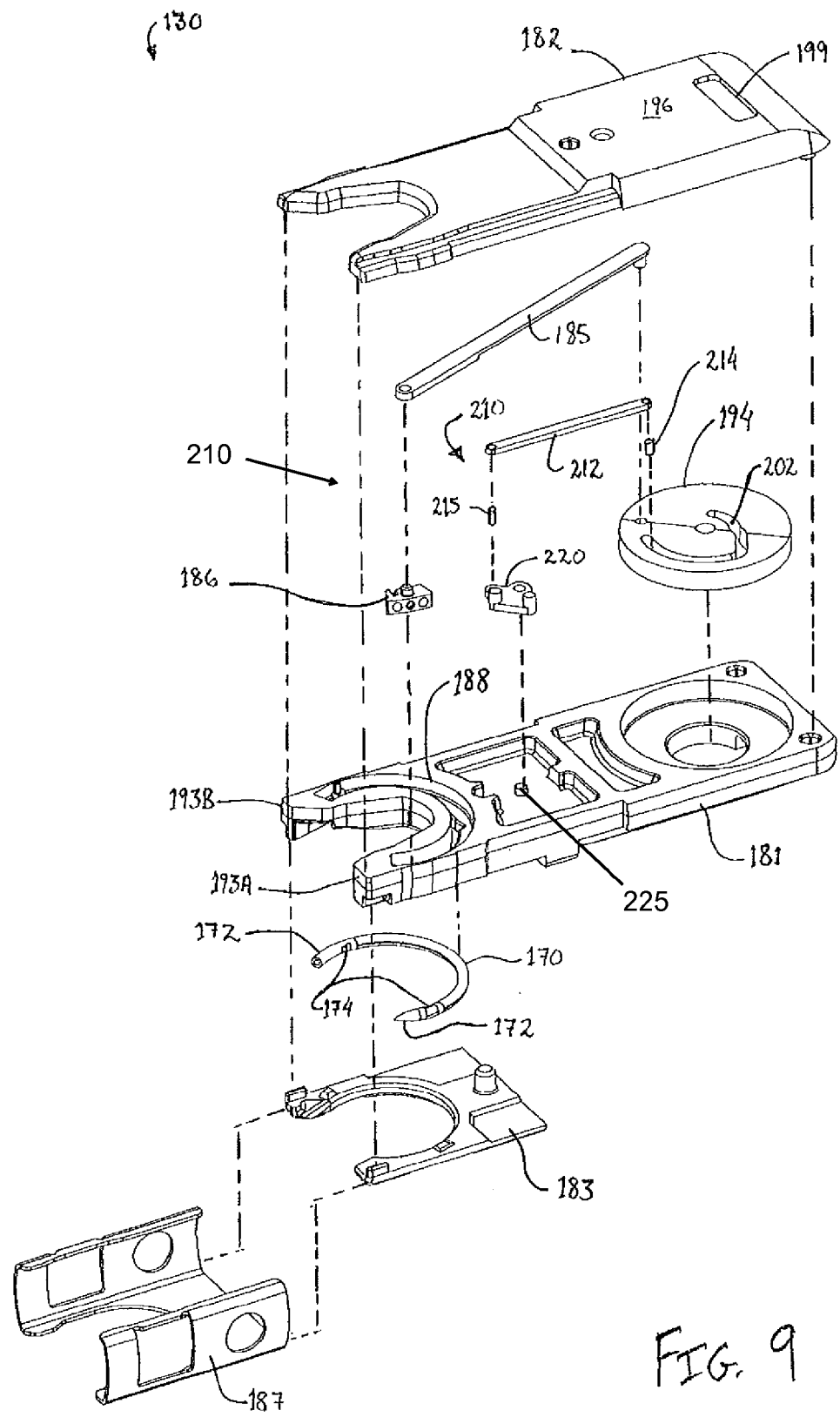
FIG. 9 depicts an exploded view of the cartridge of FIG. 7.

FIGS. 7-9 shown an alternative needle applier cartridge (130) that may be used with instrument (2) described above. It should be understood that needle applier cartridge (130) of the present example is substantially the same as needle applier cartridge (30) described above, unless otherwise noted herein, such that needle applier cartridge (130) may be readily used in place of needle applier cartridge (30). In particular, like needle applier cartridge (30), needle applier cartridge (130) comprises a cartridge body (190). Cartridge body (190) comprises a lower face (191) that is adapted to engage lower jaw (51); and an upper face (196) that is adapted to engage upper jaw (56).

Like with cartridge body (90) described above, poke-yoke features on cartridge body (190) prevent improper insertion of cartridge body (190) into cartridge receiving assembly (50). For instance, lower face (191) has a pair of longitudinal notched shoulders (192) that are dimensioned to interface and mate with rails (52). In contrast, upper face (196) is asymmetrical relative lower face (191) and lacks shoulder notches, so upper face (196) would interfere with rails (52) if cartridge body (190) were inserted upside-down in cartridge receiving assembly (50). In another instance, the geometry of a proximal face (198) of cartridge body (190) is vertically asymmetrical and thus prevents cartridge body (190) from being inserted upside-down between jaws (51, 56). In this example, proximal face (198) comprises a curved surface that gently transitions to upper face (196), which matches similar geometry in cartridge receiving assembly (50); while the transition to lower face (191) has a tighter radius. Of course, a variety of other asymmetrical aesthetic geometries could also be employed that could contribute to the visual appearance and/or poke-yoke aspects of cartridge body (190).

Carriage body (190), like carriage body (90), also comprises arms (193A, 193B), which define a generally U-shaped distal end on cartridge body (190). A slot (195) and rotary input (194) are aligned and dimensioned to receive the key (48) while cartridge body (190) is being slid into cartridge receiving assembly (50). When cartridge body (90) is fully seated into cartridge receiving assembly (50), a step (199) aligns with and receives tooth (59) to latch cartridge body (190) in cartridge receiving assembly (50).

Key (48) also aligns with rotary input (194), thereby providing a torsional interface that rotationally couples pinion (47) and rotary input (194). In use, a needle (170) exits arm (193A) and enters arm (193B).

As shown in FIGS. 7-9, cartridge body (190) further comprises a lower body (181), an upper body (182), a needle (170), and a needle cover (183). A needle driver (186), rotary input (194), a link (185), and a guide assembly (210) are captured between lower body (181) and upper body (182). Needle (170) has a leading end (171) and a length of suture (not shown) extending from a trailing end (172). Needle (170) orbits in a circular path defined by a needle track (184) and between arms (193A, 193B). Needle (170) includes notches (174) that are configured to facilitate engagement between needle driver (186) and needle (170). Needle (170) is captured in needle track (184) by needle cover (183). A cage (187) slides over bodies (181, 182) and needle cover (183) to attach needle cover (183) against lower body (181).

Unlike needle applier cartridge (30) described above, needle applier cartridge (130) of the present example further comprises guide assembly (210). As will be understood, guide assembly (210) is generally configured to aid the distal end of link (185) in movement along a generally semi-circular path. Guide assembly (210) comprises a guide link (212) and a guide member (220). Guide link (212) comprises an elongate rigid beam and is generally configured to transfer rotary movement of rotary input (194) to guide member (220) as will be described in greater detail below.

Guide link (212) comprises a proximal pin (214) and a distal pin (215). Proximal pin (214) is configured to engage a cam path (202) that is formed in at least a portion of rotary input (194). Similarly, distal pin (215) is received in a first opening (222) of guide member (220). As will be understood, guide link (212) is configured such that proximal pin (214) is directed along the path defined by cam path (202) of rotary input (194) to move guide member (220) along a predetermined path via distal pin (215).

Figure 10:
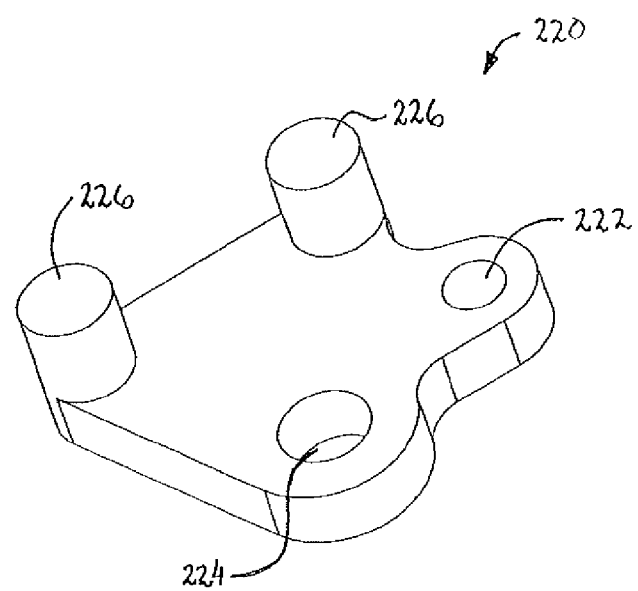
FIG. 10 depicts a perspective view of a guide member of the cartridge of FIG. 7.

Guide member (220) is best seen in FIG. 10. As can be seen, guide member (220) comprises first opening (222), a second opening (224), and a pair of guide protrusions (226). As described above, first opening is configured to receive distal pin (215) of guide link (212). Second opening (224) is configured to receive a post (225) extending upwardly from lower body (181) to permit guide member (220) to pivot about post (225). Guide protrusions (226) are configured to direct the distal portion of link (185) as guide member (220) is pivoted about post (225). In particular, when needle applier cartridge (130) is assembled, link (185) is laterally disposed between each protrusion (226) such that protrusions (226) cooperate to provide guidance to the distal portion of link (185) as guide member (220) is pivoted by guide link (212).

Figure 11:
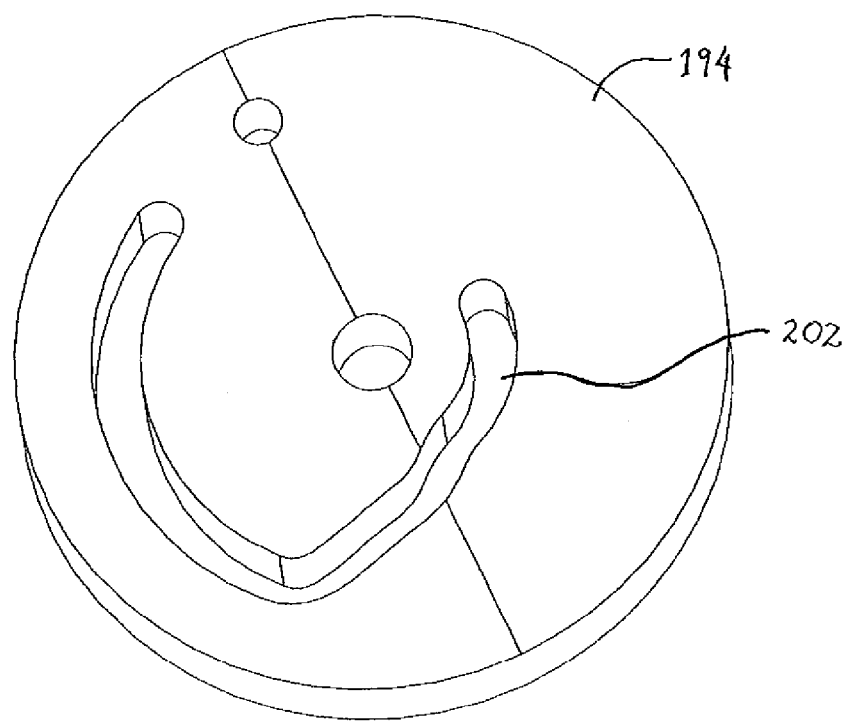
FIG. 11 depicts a perspective view of a cam wheel of the cartridge of FIG. 7.

FIG. 11 shows cam path (202) of rotary input (194) in greater detail. As can be seen, cam path (202) has a predetermined shape that corresponds to a particular travel path of guide member (220). In particular, as rotary input (194) is rotated, proximal pin (214) will travel along the path defined by cam path (202) causing guide link (212) to move. At least some movement of guide link (212) will then be transferred to guide member (220) by distal pin (215) in the form of a pivoting motion. Thus, the pivoting of guide member (220) is determined by the predetermined shape of cam path (202). This pivoting corresponds to a path of link (185) that is required to drive needle driver (186) along a generally semi-circular path.

Figure 12A:
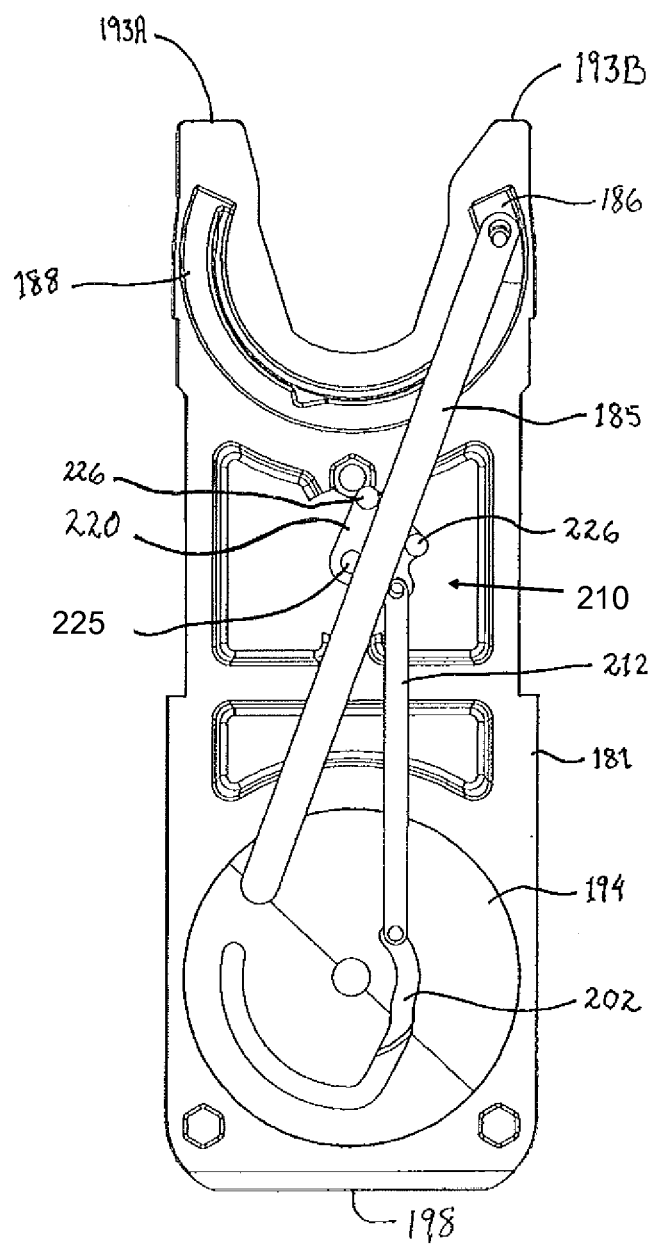
FIG. 12A depicts a top plan view of the cartridge of FIG. 7, with external components removed to reveal internal components, with the cartridge at a first stage of actuation.

FIGS. 12A-12D illustrate an example of a drive stroke of the transmission in cartridge body (190) for driving needle (170) in a circular, orbital path. Needle driver (186) rides in a carrier track (188) and extends into needle track (184) to engage and drive needle (170). Link (185) connects rotary input (194) to needle driver (186) and guide assembly (210) ensures the distal end of link (185) remains on a generally semi-circular path to drive needle driver (186). FIG. 12A shows needle driver (186) positioned at one end of its stroke in carrier track (188). In this position, needle (170) is in its retracted position and completely contained in needle track (184).

Figure 12B:
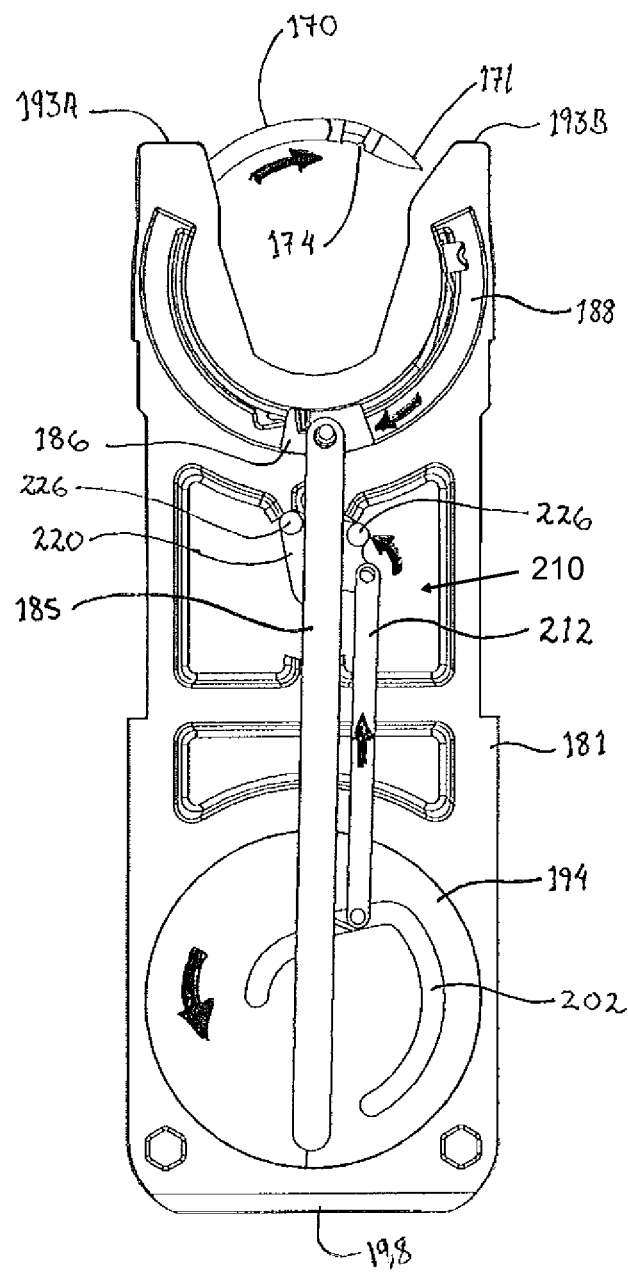
FIG. 12B depicts a top plan view of the cartridge of FIG. 7, with external components removed to reveal internal components, with the cartridge at a second stage of actuation.

To initiate movement of needle (170) when needle applier cartridge (130) is equipped with instrument (2), a surgeon will depress first input (12). When first input (12) is depressed, closing the trigger, needle driver (186) will be actuated through its drive stroke where it orbits along an angular range of motion at least about 180 degrees clockwise (in the views shown in FIGS. 12A-12D) to a driven position. As shown in FIG. 12B, counterclockwise rotation of rotary input (194) will drive needle driver (186) clockwise along carrier track (188), thereby driving needle (170) clockwise. Correspondingly, cam path (202) will move guide link (212) along a substantially straight path that is aligned with the longitudinal axis of guide link (212) to pivot guide member (220), thereby guiding the distal portion of link (185) to smoothly transition from the orientation shown in FIG. 12A to the orientation shown in FIG. 12B.

Figure 12C:
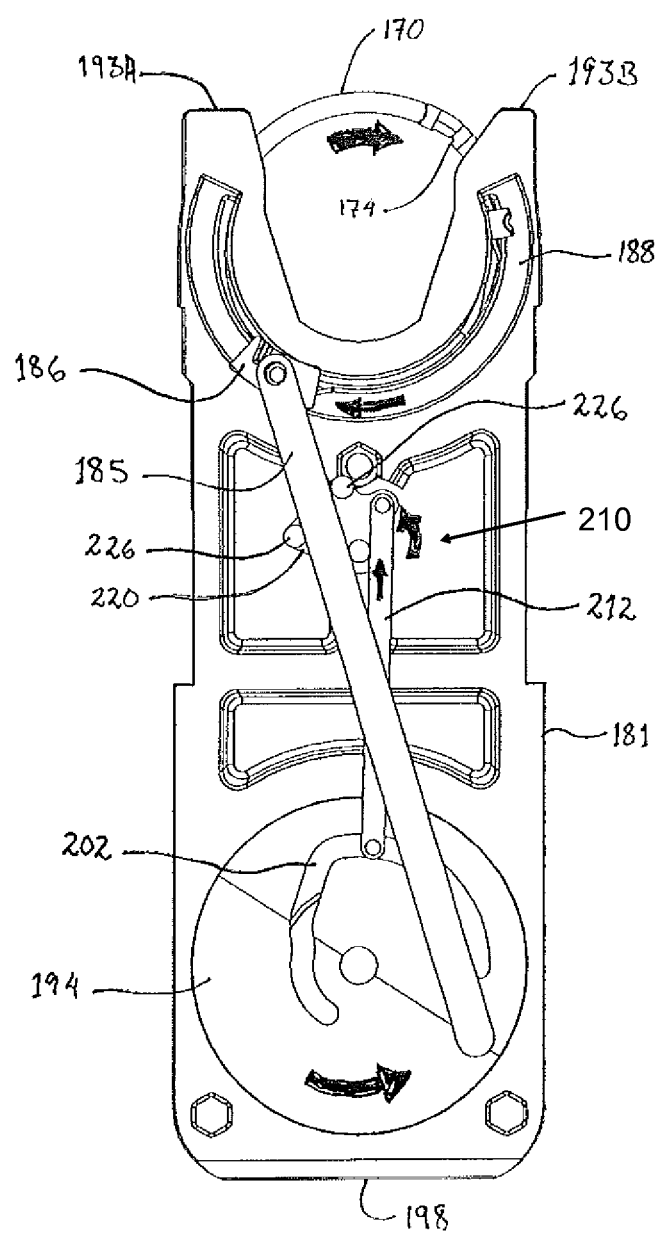
FIG. 12C depicts a top plan view of the cartridge of FIG. 7, with external components removed to reveal internal components, with the cartridge at a third stage of actuation.
Figure 12D:
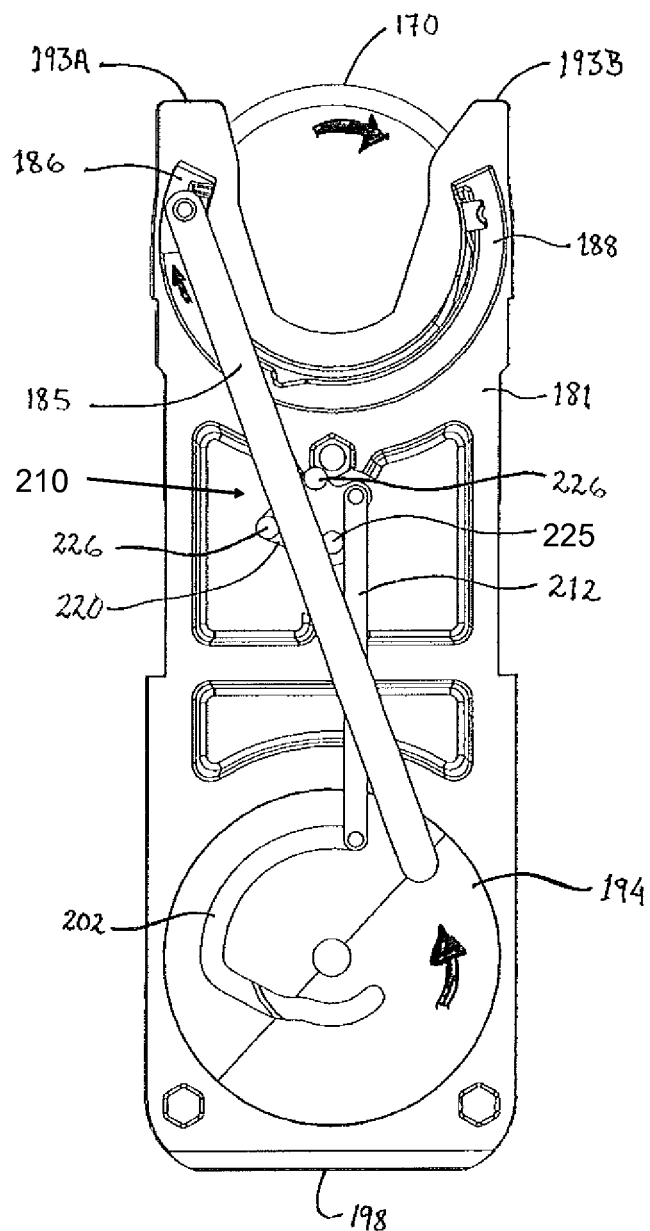
FIG. 12D depicts a top plan view of the cartridge of FIG. 7, with external components removed to reveal internal components, with the cartridge at a fourth stage of actuation.

As shown in FIG. 12C, continued counterclockwise rotation of the rotary input (194) will continue to drive needle driver (186) and thereby drive needle (170) clockwise until it reaches the other end of its stroke in carrier track (188). Guide assembly (210) will correspondingly direct the distal portion of link (185) along the path of carrier track (188) via pivoting of guide member (220) by interaction between guide link (212) and cam path (202). Again, cam path (202) drives guide link along a substantially straight path that is aligned with the longitudinal axis of guide link (212) to pivot guide member (220) in the transition from the state shown in FIG. 12B to the state shown in FIG. 12C. In this example, the drive stroke rotates the needle (170) in its circular path along an angular range of about 180 degrees (e.g., from the position shown in FIG. 12A to the position shown in FIG. 12D). In the present example, cam path (202) is configured such that guide link (212) and guide member (220) remain substantially stationary while link (185), needle driver (186), and needle (170) travel along the remainder of track (188) as shown in the transition from FIG. 12C to FIG. 12D.

When first input (12) is released and the spring return opens the trigger, needle driver (186) disengages needle (170) and reciprocates through its return stroke where it orbits along an angular range of motion about 180 degrees counterclockwise back to the return position shown in FIG. 12A. For the return stroke, other than needle (170) remaining stationary, the above described sequence of movement of link (185) and guide assembly (210) is reversed by rotating rotary input (194) in a clockwise direction. Clockwise rotation of rotary input (194) will translate needle driver (186) counterclockwise in carrier track (188). Such motion of needle driver (186) will be caused by link (185) and guide assembly (210) as similarly described above, but in a reverse direction. Needle driver (186) is disengaged from needle (170) during the return stroke until needle driver (186) reaches the end of the return stroke. Needle driver (186) will re-engage needle (186) upon completing the return stroke. Thus, a sequence of drive and return strokes will rotate the needle (170) in a circular path.

When first input (12) is depressed again closing the trigger, needle driver (186) will again be actuated through its drive stroke where it orbits along an angular range of motion about 180 degrees clockwise to the driven position. During the drive stroke, needle driver (186) engages the distal end of needle (170) and will in unison drive needle (170) orbitally along an angular range of motion about 180 degrees back to its retracted position. The suture will follow needle (170) and will thus be threaded through the pierced tissue.

When first input (12) is again released and the spring return opens the trigger, needle driver (186) again reciprocates through its return stroke where it orbits along an angular range of motion about 180 degrees counterclockwise back to its returned position as shown in FIG. 12A. During the return stroke, needle driver (186) slides over needle (170). Thus, needle (170) is driven in a complete circular path spanning an angular range of 360° in response to first input (12) being actuated twice. The sequence may be repeated as needed by the surgeon to achieve the desired suturing task.

Although not shown, it should be understood that in some examples needle applier cartridge (130) also comprises one or more features that ensure that the orbital motion of needle (170) is in just one single angular direction. Such features may be constructed and operable in accordance with at least some of the teachings of U.S. patent application Ser. No. 14/298,038, entitled "Circular Needle Applier with Cleats," filed Jan. 30, 2015, now U.S. Pat. No. 9,375,212, issued Jun. 28, 2016, the disclosure of which is incorporated by reference herein.

Figure 13:
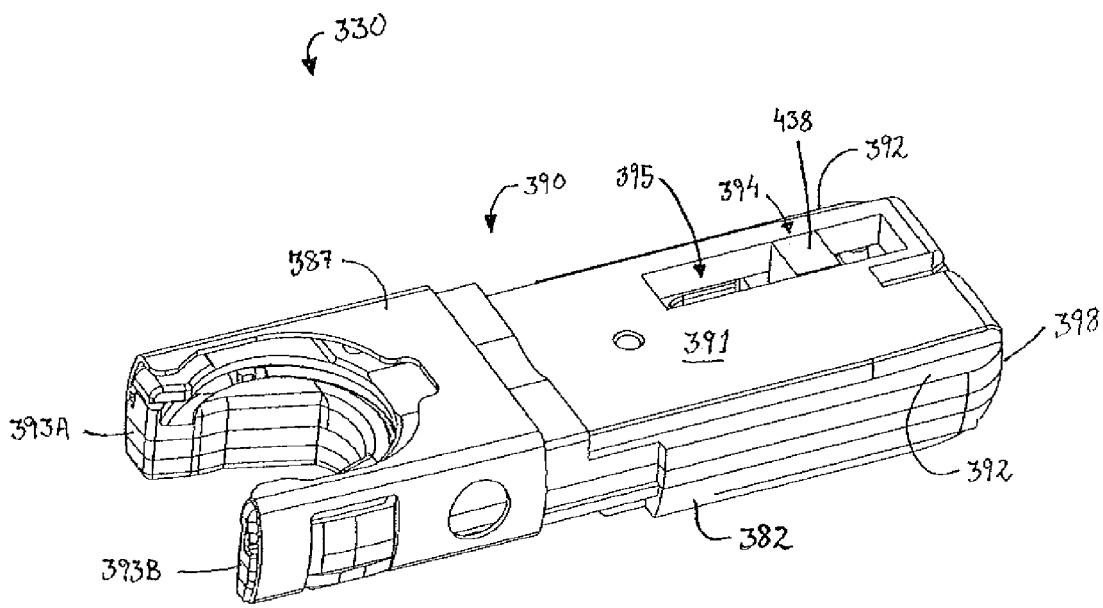
FIG. 13 depicts a perspective view of another exemplary cartridge configured for receipt in the cartridge receiving assembly of FIG. 2A.
Figure 14:
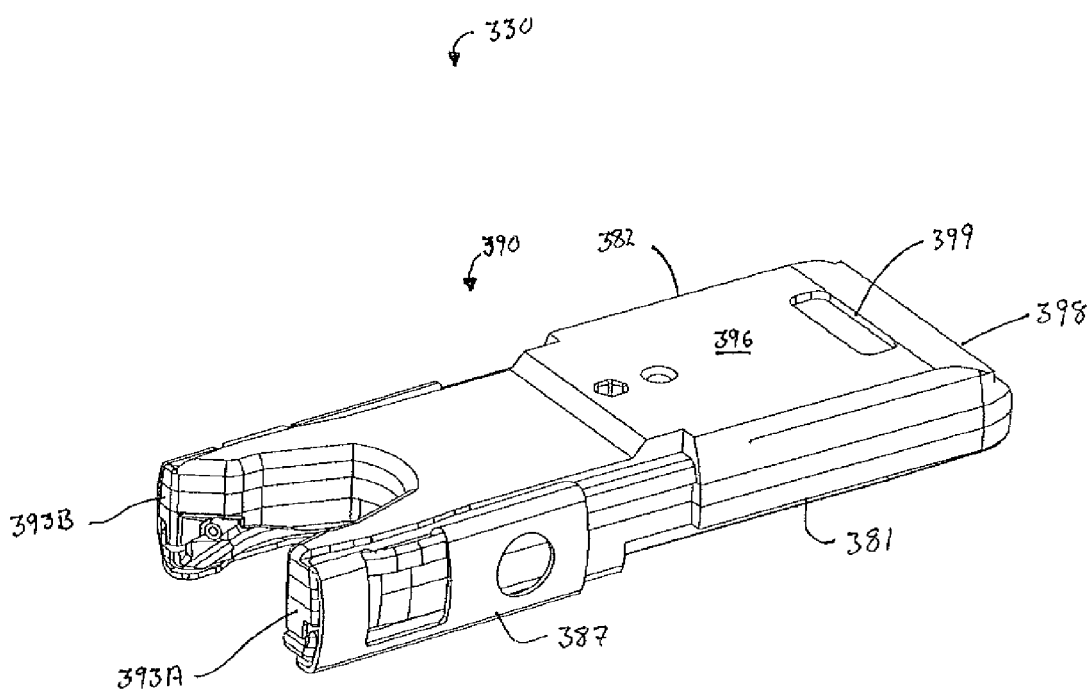
FIG. 14 depicts another perspective view of the cartridge of FIG. 13.
Figure 15:
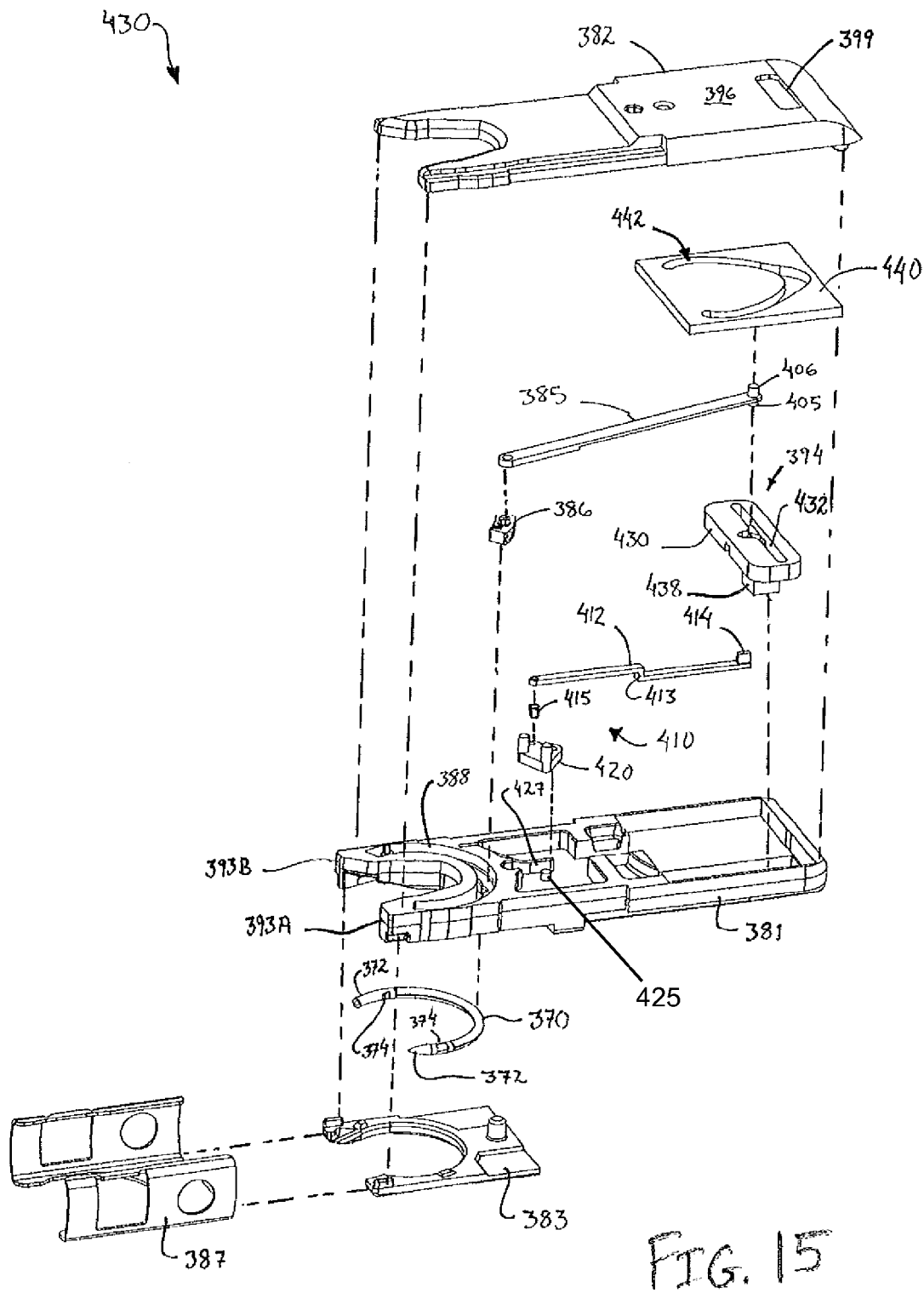
FIG. 15 depicts an exploded view of the cartridge of FIG. 13.

B. Exemplary Alternative Needle Applier Cartridge with Linearly Reciprocating Input FIGS. 13-15 illustrate another example of an alternative needle applier cartridge (330) that may be used with instrument (2) described above. It should be understood that needle applier cartridge (330) of the present example is substantially the same as needle applier cartridge (30) described above, unless otherwise noted herein. In particular, like needle applier cartridge (30), needle applier cartridge (330) comprises a cartridge body (390). Cartridge body (390) comprises a lower face (391) that is adapted to engage lower jaw (51); and an upper face (396) that is adapted to engage upper jaw (56).

Needle applier cartridge (330) is configured for use with a variation of instrument (10) where cartridge receiving assembly (50) provides a linear drive output rather than a rotary drive output. In particular, cartridge (330) is configured for use with a variation of instrument (10) where cartridge receiving assembly (50) lacks rack (45), pinion (47), and key (48). Instead, distal end (28C) of drive rod (28) couples with an adapter (not shown) that mates with a linear drive input (394) of cartridge (330) as will be described in greater detail below. Longitudinal reciprocation of drive rod (28) is thus communicated directly to linear drive input (394) as longitudinal reciprocation via the adapter. Various suitable forms that such an adapter may take will be apparent to those of ordinary skill in the art in view of the teachings herein.

Like with cartridge body (90) described above, poke-yoke features on cartridge body (390) prevent improper insertion of cartridge body (390) into cartridge receiving assembly (50). For instance, lower face (391) has a pair of longitudinal notched shoulders (392) that are dimensioned to interface and mate with rails (52). In contrast, upper face (396) is asymmetrical relative lower face (391) and lacks shoulder notches, so upper face (396) would interfere with rails (52) if cartridge body (390) were inserted upside-down in cartridge receiving assembly (50). In another instance, the geometry of a proximal face (398) of cartridge body (390) is vertically asymmetrical and thus prevents cartridge body (390) from being inserted upside-down between jaws (51, 56). In this example, proximal face (398) comprises a curved surface that gently transitions to upper face (396), which matches similar geometry in cartridge receiving assembly (50); while the transition to lower face (391) has a tighter radius. Of course, a variety of other asymmetrical aesthetic geometries could also be employed that could contribute to the visual appearance and/or poke-yoke aspects of cartridge body (390).

Carriage body (390), like carriage body (90), also comprises arms (393A, 393B), which define a generally U-shaped distal end on cartridge body (390). However, unlike carriage body (90) described above, carriage body (390) includes a linear input (394) that is disposed within slot (395). Slot (395) and linear input (394) are aligned and dimensioned to receive the adapter (not shown) that is coupled with distal end (28C) of drive rod (28) while cartridge body (390) is being slid into cartridge receiving assembly (50). When cartridge body (390) is fully seated into cartridge receiving assembly (50), a step (399) aligns with and receives tooth (59) to latch cartridge body (390) in cartridge receiving assembly (50). The adapter (not shown) that is coupled with distal end (28C) of drive rod (28) also aligns with linear input (394), thereby providing a slidable interface that linearly couples the adapter and input (394). In use, a needle (370) exits arm (393A) and enters arm (393B).

As shown in FIGS. 13-15, cartridge body (390) further comprises a lower body (381), an upper body (382), a needle (370), and a needle cover (383). A needle driver (386), linear input (394), a link (385), and a guide assembly (410) are captured between lower body (381) and upper body (382). Needle (370) has a leading end (371) and a length of suture (not shown) extending from a trailing end (372). Needle (370) orbits in a circular path defined by a needle track (384) and between arms (393A, 393B). Needle (370) includes notches (374) that are configured to facilitate engagement between needle driver (386) and needle (370). Needle (370) is captured in needle track (384) by needle cover (383). A cage (387) slides over bodies (381, 382) and needle cover (383) to attach needle cover (383) against lower body (381).

Figure 16:
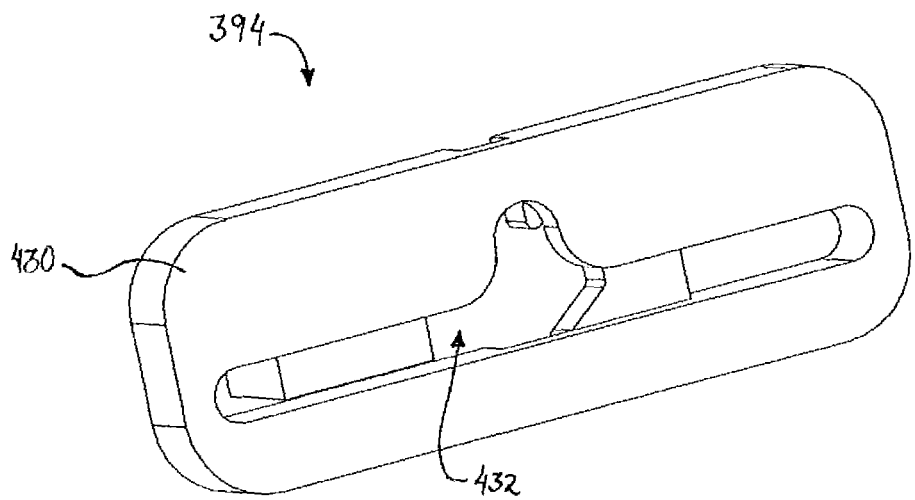
FIG. 16 depicts a perspective view of a translating cam member of the cartridge of FIG. 13.
Figure 17:
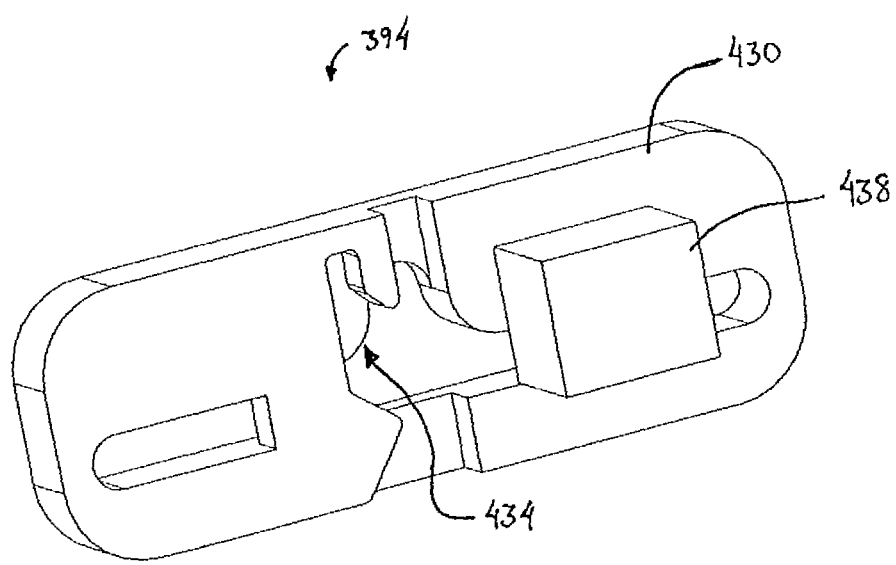
FIG. 17 depicts another perspective view of the translating cam member of FIG. 16.

As is best seen in FIGS. 15-17, linear input (394) comprises a body (430) and an actuation block (438). Body (430) has two separate cam paths (432, 434). A first cam path (432) (as best seen in FIG. 16) is configured to receive a lower cam pin (405) of link (385). As will be described in greater detail below, first cam path (432) is generally configured to drive link (385) longitudinally relative to cartridge body (390) while accommodating lateral movement of the proximal end of drive ling (385). A second cam path (434) (as best seen in FIG. 17) is configured to receive a cam member (414) of a guide link (412) of guide assembly (410). As will be described in greater detail below, second cam path (434) is generally configured to maintain guide link (412) in a longitudinally straight orientation relative to cartridge body (390).

Actuation block (438) of linear input (394) is generally configured to communicate with the adapter (not shown) that is coupled with distal end (28C) of drive rod (28) to linearly drive linear input (394). Actuation block (438) of the present example comprises a generally rectangular shape protruding from body (430). Although not shown, it should be understood that in some examples actuation block (438) may include various other features suitable for permitting communication of motive force between the adapter (not shown) that is coupled with distal end (28C) of drive rod (28) and actuation block (438).

Figure 20:
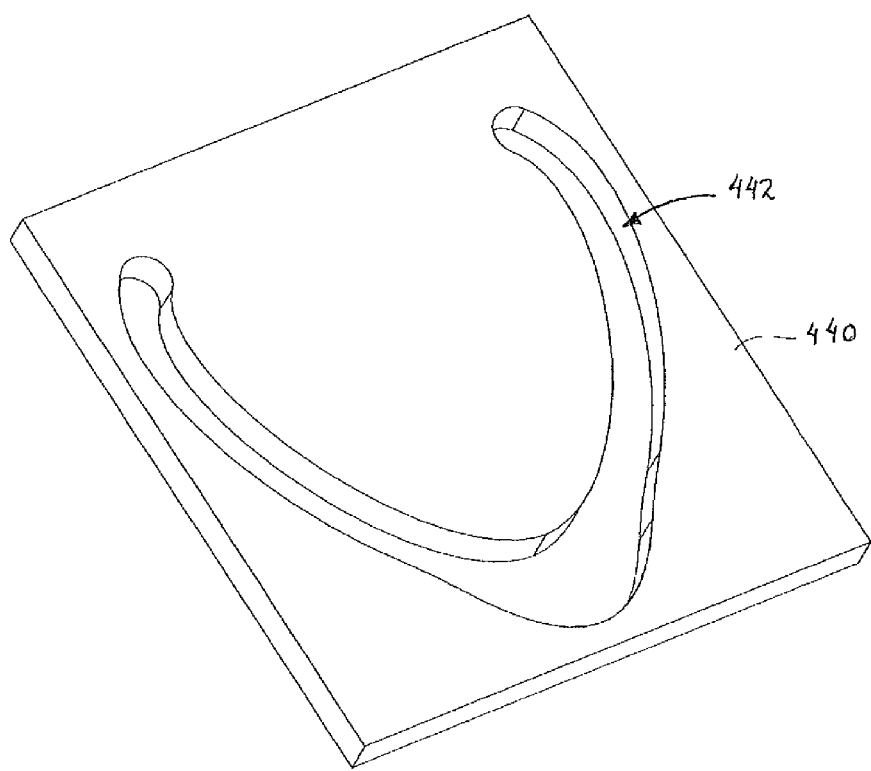
FIG. 20 depicts a perspective view of a cam plate of the cartridge of FIG. 13.

Again referring to FIG. 15, cartridge body (390) further includes a cam plate (440) that drives lateral translation of link (385). As best seen in FIG. 20, cam plate (440) includes a third cam path (442). Third cam path (442) has a generally wishbone shape that is configured to drive the proximal end of link (385) laterally. In particular, third cam path (442) is configured to receive an upper cam pin (406) of link (385). As will be described in greater detail below, the combination of first cam path (432) and third cam path (442) operates to laterally and longitudinally translate the proximal end of link (385) to drive needle driver (386) along a generally semi-circular path.

Also unlike needle applier cartridge (30) described above, needle applier cartridge (330) of the present example further comprises guide assembly (410). As will be understood, guide assembly (410) is generally configured to guide the distal end of link (385) in movement along a generally semi-circular path. Guide assembly (410) comprises a guide link (412), a guide member (420), and a resilient member (427). Guide link (412) comprises an elongate rigid beam and is generally configured to transfer guide or drive guide member (420) as will be described in greater detail below. Although guide link (412) of the present example is shown as having a step (413) disposed near the longitudinal center point of guide link (412), it should be understood that this feature is merely optional and may be omitted in some examples.

Figure 19:
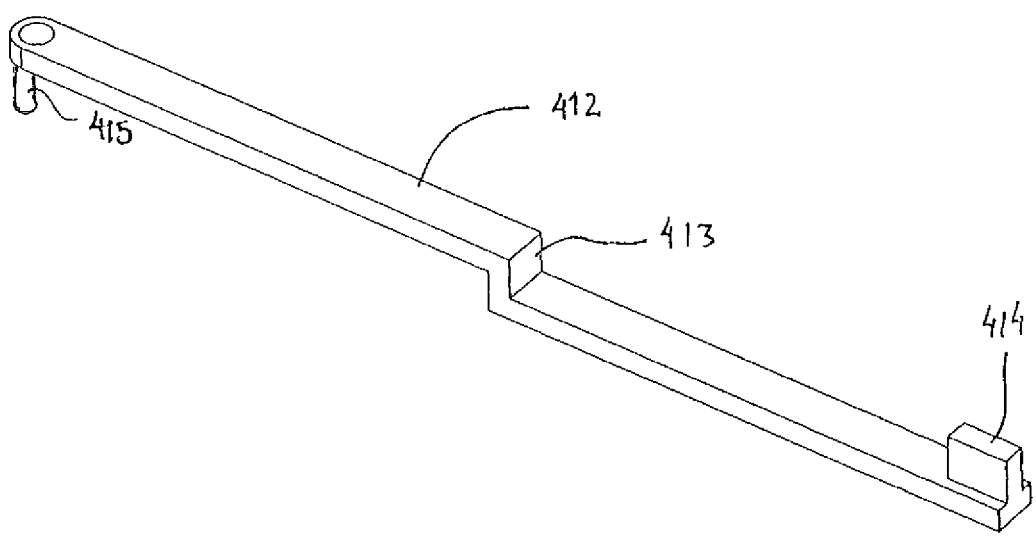
FIG. 19 depicts a perspective view of a guide rod of the cartridge of FIG. 13.

As best seen in FIG. 19, guide link (412) comprises cam member (414) and a distal pin (415). As described above, cam member (414) is configured to engage second cam path (434) disposed in body (430) of linear input (394). Cam member (414) is generally rectangular in shape, although any other suitable shape may be used. Distal pin (415) is received in a first opening (422) of guide member (420). As will be understood, guide link (412) is configured such that cam member (414) is directed along the path defined by second cam path (434) of linear input (394) to drive or hold guide member (420) along a predetermined path via distal pin (415).

Figure 18:
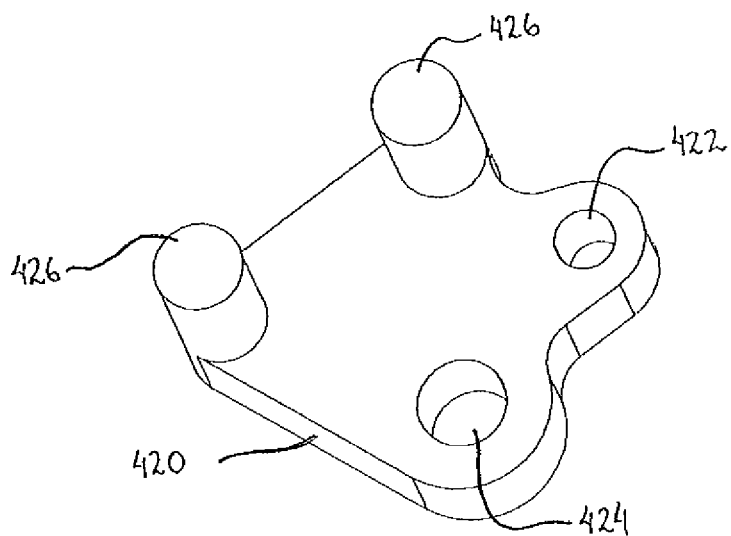
FIG. 18 depicts a perspective view of a guide member of the cartridge of FIG. 13.

Guide member (420) is best seen in FIG. 18. As can be seen, guide member (420) comprises first opening (422), a second opening (424), and a pair of guide protrusions (426). As described above, first opening (422) is configured to receive distal pin (415) of guide link (412). Second opening (424) is configured to receive a post (425) extending upwardly from lower body (381) to permit guide member (420) to pivot about post (425). Guide protrusions (426) are configured to direct the distal portion of link (385) as guide member (420) is pivoted about post (425). In particular, when needle applier cartridge (330) is assembled, link (385) is laterally disposed between each protrusion (426) such that protrusions (426) cooperate to provide guidance to the distal portion of link (385) as guide member (420) pivots.

Figure 21A:
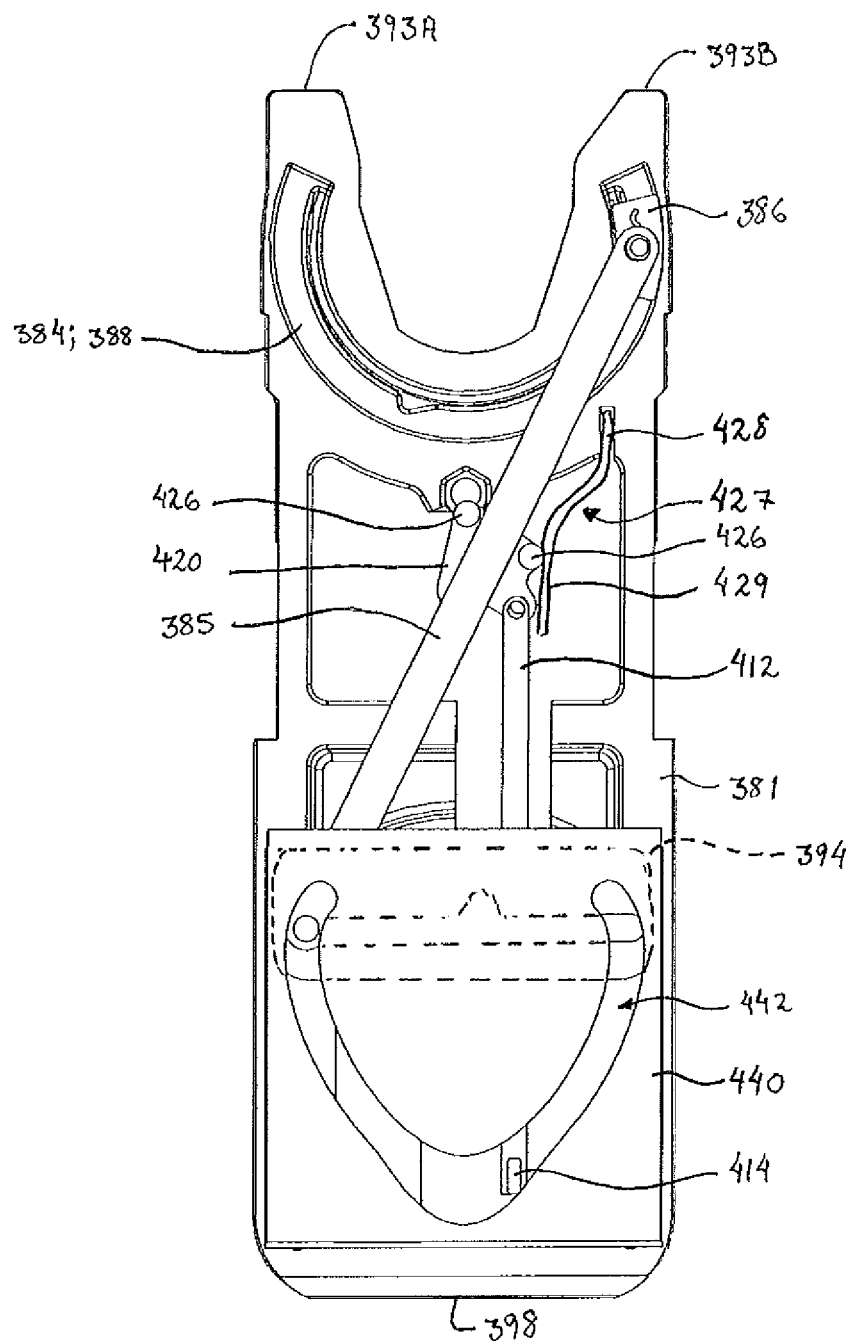
FIG. 21A depicts a top plan view of the cartridge of FIG. 13, with external components removed to reveal internal components, with the cartridge at a first stage of actuation.

As can be seen in FIG. 21A, resilient member (427) is in the form of a leaf spring that has a fixed distal end (428) and a free proximal end (429). Distal end (428) is fixedly secured to a receiving feature of lower body (381). Proximal end (429) is relatively free to move relative to lower body (381). In particular, resilient member (427) has a shape that permits proximal end (429) to resiliently bear against the side of guide member (420). As will be understood, guide link (412) is only configured to allow guide member (420) to pivot through a particular range of motion. However, in some instances it may be desirable for guide member (420) to pivot through a range of motion beyond the range of motion supplied or governed by guide link (412). Accordingly, proximal end (429) of resilient member (427) may provide pivoting of guide member (420) when such pivoting is not driven by guide link (412).

FIGS. 21A-21D illustrate an example of a drive stroke of the transmission in cartridge body (390) for driving needle (370) in a circular, orbital path. Needle driver (386) rides in a carrier track (388) and extends into needle track (384) to engage and drive needle (370). Link (385) connects linear input (394) to needle driver (386) and guide assembly (410) ensures that the distal end of link (385) remains on a generally semi-circular path to drive needle driver (386). FIG. 21A shows needle driver (386) positioned at one end of its stroke in carrier track (388). In this position, needle (170) is in its retracted position and completely contained in needle track (384).

Also in the in the position shown in FIG. 21A, linear input (394) is disposed distally within to lower body (381). Correspondingly, the distal end of link (385) is disposed distally in third cam path (442) of cam plate (440). It should be understood that in this position, the distal end of link (385) is held in the distal position shown in FIG. 21A by first cam path (432) of linear input (394). The distal end of link (385) is oriented toward one end of carrier track (388) as governed by guide member (420). In particular, link (385) is disposed between guide protrusions (426). The proximal end of link (385) will be governed by a location at which third cam path (442) overlaps with first cam path (432) as linear input (394) reciprocates longitudinally within lower body (381) throughout the sequence shown in FIGS. 21A-21D.

Figure 21B:
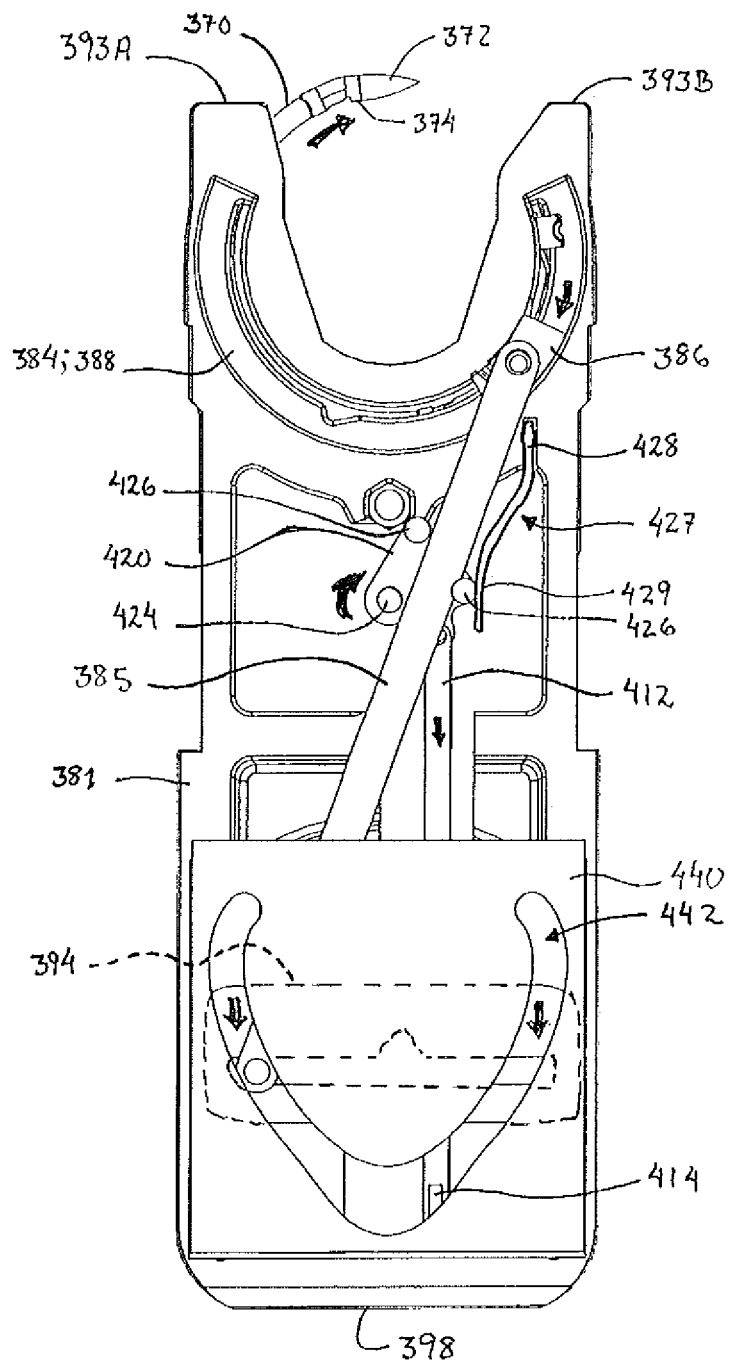
FIG. 21B depicts a top plan view of the cartridge of FIG. 13, with external components removed to reveal internal components, with the cartridge at a second stage of actuation.

To initiate movement of needle (370) when needle applier cartridge (330) is equipped with instrument (2), a surgeon will depress first input (12). When first input (12) is depressed, closing the trigger, needle driver (386) will be actuated through its drive stroke where it orbits along an angular range of motion at least about 180 degrees counterclockwise to a driven position. As shown in FIG. 21B, proximal translation of linear input (394) will drive the proximal end of link (385) proximally and laterally via engagement with first and third cam paths (432, 442). This movement causes link (385) to drive needle driver (386) clockwise along carrier track (388), thereby driving needle (370) clockwise. Link (385) bears against guide member (420) during this motion such that guide member (420) rotates slightly clockwise, against the bias provided by resilient member (427). As guide member (420) rotates clockwise, guide member (420) drives guide link (412) proximally. Second cam path (434) allows guide link (412) to freely translate proximally but maintains a straight longitudinal alignment of guide link (412).

Figure 21C:
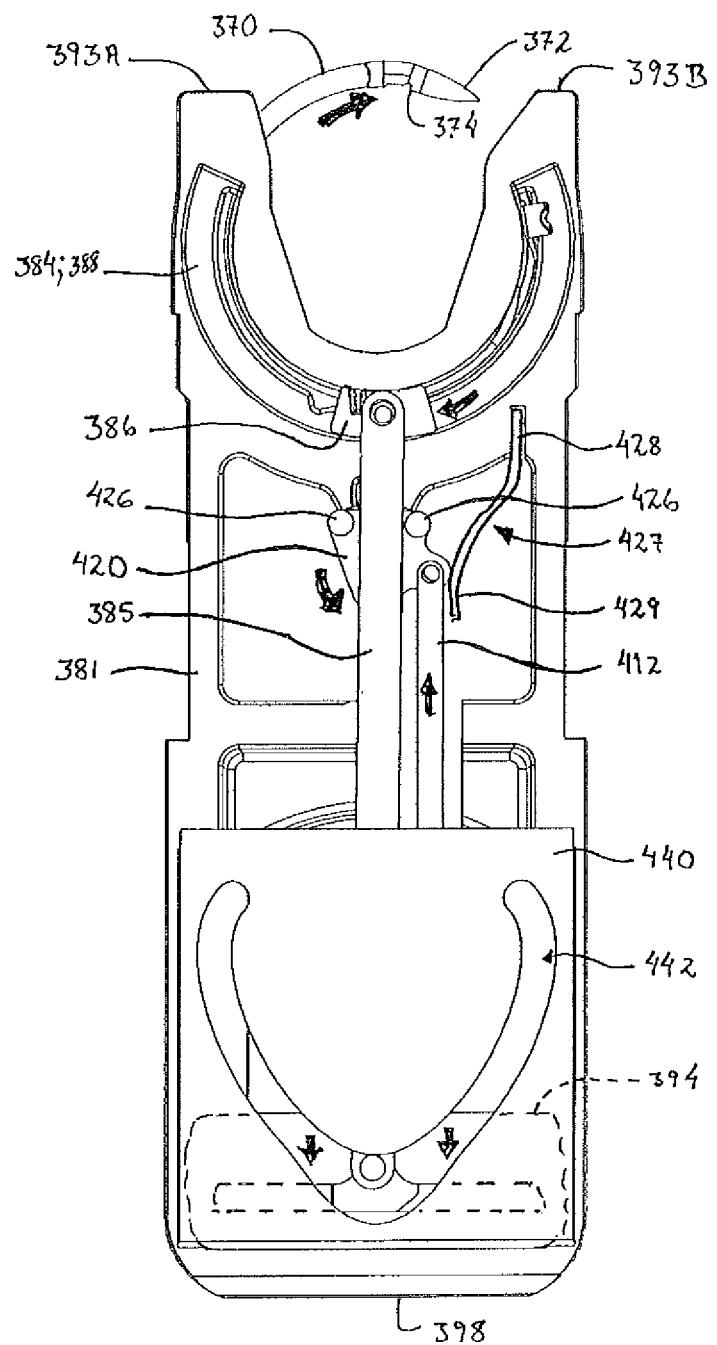
FIG. 21C depicts a top plan view of the cartridge of FIG. 13, with external components removed to reveal internal components, with the cartridge at a third stage of actuation.

When first input (12) of instrument (2) is fully depressed, linear input (394) is positioned at a fully proximal position as shown in FIG. 21C. When linear input (394) is in the fully proximal position, needle driver (386) is only halfway through its drive stroke. Correspondingly, the proximal end of link (385) is disposed at the apex of the wishbone shape of third cam path (442) and at the central region of first cam path (442). At this stage, guide member (420) has been pivoted counterclockwise by resilient member (427). Guide member (420) thus pulls guide link (412) distally. Again, second cam path (434) allows guide link (412) to freely translate distally but maintains a straight longitudinal alignment of guide link (412).

Figure 21D:
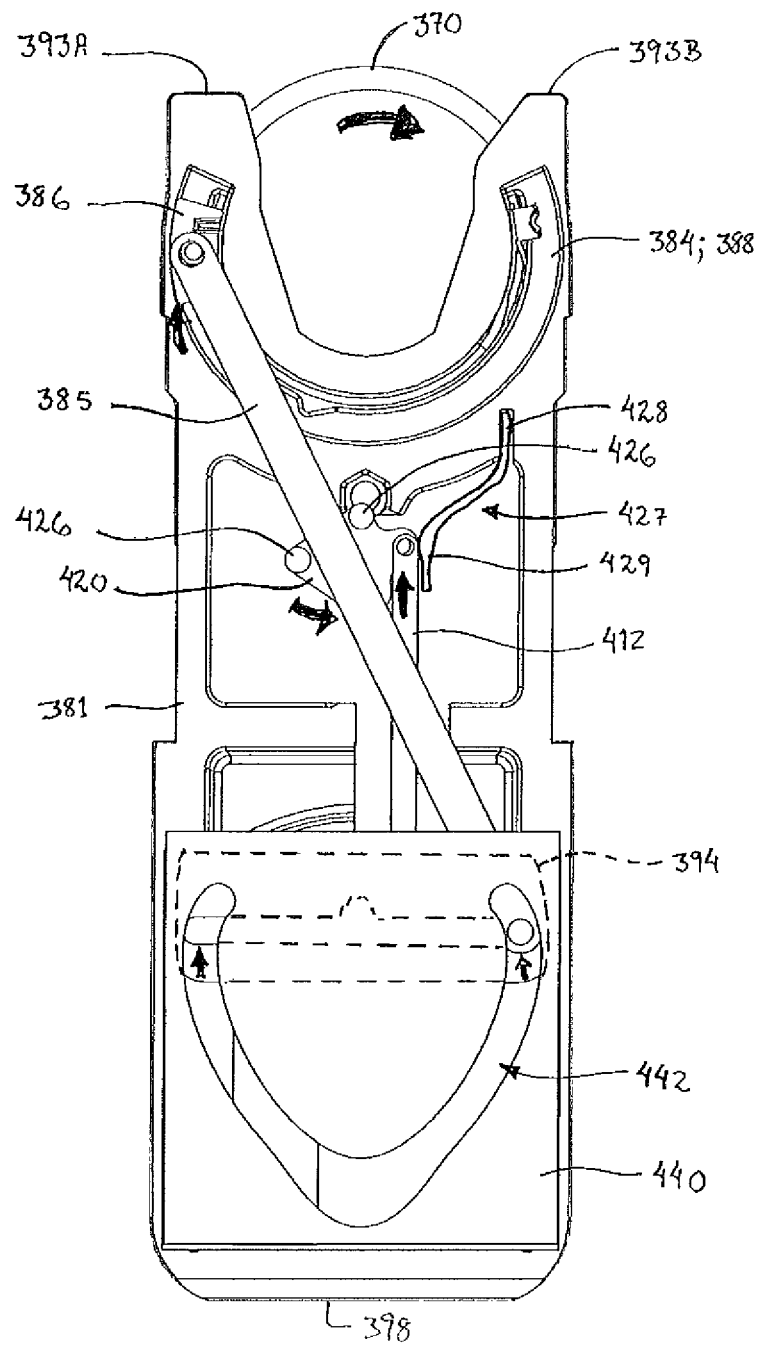
FIG. 21D depicts a top plan view of the cartridge of FIG. 13, with external components removed to reveal internal components, with the cartridge at a fourth stage of actuation.

Releasing first input (12), opening trigger via spring return, will result in continued movement of needle driver (386) clockwise until it reaches the other end of its stroke in carrier track (388) as shown in FIG. 21D. Guide assembly (410) will correspondingly direct link (385) along the path of carrier track (388) via pivoting of guide member (420) by resilient member (427). In this example, the drive stroke rotates the needle (370) in its circular path along an angular range of about 180 degrees (e.g., from the position shown in FIG. 21A to the position shown in FIG. 21D). At this stage, guide member (420) has been further pivoted counterclockwise by resilient member (427). Guide member (420) thus pulls guide link (412) further distally. Again, second cam path (434) allows guide link (412) to freely translate distally but maintains a straight longitudinal alignment of guide link (412).

It should be understood that a full actuation of first input (12) (e.g., pull and release) will result in needle (370) progressing only about 180 degrees through its full 360 degree stroke. To fully actuate needle (370) through its full 360 degree stroke, first input (12) will first be depressed again. When first input (12) is again depressed, closing the trigger, needle driver (386) reciprocates through a return stroke where it orbits along an angular range of motion about 180 degrees clockwise back to the position shown in FIG. 21A. For the return stroke, the sequence is be reversed with linear input (394) first translating proximally. As similarly described above, proximal translation of linear input (394) will translate needle driver (386) counterclockwise in carrier track (388) as the proximal end of link (385) travels in the reverse direction through first and third cam paths (432, 442). When first input (12) of instrument (2) is fully depressed, needle driver (386) may be progressed through the remainder of the return stroke by releasing first input (12), opening the trigger via spring return. As similarly described above, release of first input (12) will cause distal translation of linear input (394) continuing to drive the distal end of link (385) in the reverse direction through first and third cam paths (432, 442). It should be understood that needle driver (386) is disengaged from needle (370) during the return stroke until needle driver (386) reaches the end of the return stroke. Needle driver (386) will re-engage needle (370) upon completing the return stroke.

As cartridge (330) transitions through the return stroke, with the drive components of cartridge (330) transitioning from the positions shown in FIG. 21D back to the positions shown in FIG. 21A while needle (370) remains in the position shown in FIG. 21D, guide member (420) will need to rotate clockwise against the bias provided by resilient member (427). To assist in overcoming this bias, cam member (414) of guide link (412) may engage a complementary feature of second cam path (434) of linear input (394) that pulls link (412) proximally during proximal travel of linear input (394). As link (412) is pulled proximally, link (412) will drive guide member (420) clockwise against the bias provided by resilient member (427).

To complete the circular path of needle, first input (12) is depressed and released again, closing and opening the trigger. When first input (12) is depressed and released again, needle driver (386) will again be actuated through its drive stroke where it orbits along an angular range of motion about 180 degrees counterclockwise to the driven position. During the second drive stroke, needle driver (386) engages the distal end of needle (370) and will in unison drive needle (370) orbitally along an angular range of motion about 180 degrees back to its retracted position. The suture will follow needle (370) and will thereby be threaded through the pierced tissue.

To return needle driver (386) to the position shown in FIG. 21A and ready instrument (2) for another sequence, first input (12) is again depressed and released. When first input (12) is again depressed and released, needle driver (386) again reciprocates through its return stroke where it orbits along an angular range of motion about 180 degrees clockwise back to its returned position as shown in FIG. 21A. During the return stroke, needle driver (386) slides over needle (370). Thus, needle (370) is driven in a complete circular path spanning an angular range of 360 degrees in response to first input (12) being actuated a total of four complete times. The sequence may be repeated as needed by the surgeon to achieve the desired suturing task.

Although not shown, it should be understood that in some examples needle applier cartridge (330) also comprises one or more features that ensure that the orbital motion of needle (370) is in just one single angular direction. Such features may be constructed and operable in accordance with at least some of the teachings of U.S. patent application Ser. No. 14/298,038, entitled "Circular Needle Applier with Cleats," filed Jan. 30, 2015, now U.S. Pat. No. 9,375,212, issued Jun. 28, 2016, the disclosure of which is incorporated by reference herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body; (b) an input feature; (c) an elongate shaft extending distally from the body along a longitudinal axis; and (d) a needle applier coupled to the elongate shaft, wherein the needle applier comprises: (i) a needle, (ii) a drive assembly coupled to the needle, wherein the drive assembly comprises a link configured to drive the needle orbitally about a rotation axis that is transverse to the longitudinal axis in response to actuation of the input feature, and (iii) a guide assembly, wherein the guide assembly is in communication with the input feature and the drive assembly, wherein the guide assembly is responsive to the input feature to guide a distal portion of the link along a semi-circular path.

Example 2

The surgical instrument according to Example 1, wherein the drive assembly of the needle applier is movable through a drive stroke and a return stroke.

Example 3

The surgical instrument according to Example 2, wherein the drive assembly is configured to move through the drive stroke and the return stroke after a single actuation of the input feature.

Example 4

The surgical instrument according to any one or more of Examples 2 through 3, wherein the drive assembly is configured to move through the drive stroke after a first actuation of the input feature, wherein the drive assembly is configured to move through the return stroke after a second action of the input feature.

Example 5

The surgical instrument according to any one or more of Examples 1 through 4, wherein the needle applier further comprises a rotary input, wherein the input feature is operable to rotate the rotary input.

Example 6

The surgical instrument according to Example 5, wherein the rotary input is in communication with the drive assembly, wherein the rotary input is further in communication with the guide assembly.

Example 7

The surgical instrument according to Example 6, wherein the drive assembly is pivotably secured to the rotary input, wherein at least a portion of the guide assembly is slidably secured to the rotary input.

Example 8

The surgical instrument according to Example 7, wherein the rotary input comprises a cam feature, wherein the at least a portion of the guide assembly that is slidably secured to the rotary input is configured to slide relative to the cam feature.

Example 9

The surgical instrument according to Example 8, wherein the guide assembly is responsive to the cam feature to drive at least a portion of the drive assembly along a semi-circular path.

Example 10

The surgical instrument according to any one or more of Examples 1 through 9, wherein the needle applier further comprises a linear input, wherein the linear input is in communication with the input feature.

Example 11

The surgical instrument according to Example 10, wherein the linear input is in communication with the drive assembly, wherein the linear input is further in communication with the guide assembly.

Example 12

The surgical instrument according to Example 11, wherein the linear input is configured to separately drive the drive assembly and the guide assembly in response to a common linear motion provided by the input feature.

Example 13

The surgical instrument according to any of any one or more of Examples 10 through 12, wherein the needle applier further comprises a cam plate, wherein the cam plate comprises a cam feature, wherein the drive assembly is configured to engage the cam feature.

Example 14

The surgical instrument according to Example 13, wherein the cam feature of the cam plate has a wishbone shape.

Example 15

The surgical instrument according to any one or more of Examples 13 through 14, wherein the cam feature is configured to translate the drive assembly to drive the needle about the rotation axis.

Example 16

A needle applier cartridge configured to be coupled to a needle applying instrument, the needle applier cartridge comprising: (a) a needle; and (b) a drive assembly configured to move the needle through an orbital range of motion along a circular path, the drive assembly comprising: (i) a first link, (ii) a second link, wherein the second link is in communication with the first link, and (iii) a needle driver, wherein the needle driver is coupled to at least a portion of the first link, wherein the first link is responsive to the second link to direct the needle driver along a needle drive path.

Example 17

The needle applier cartridge according to Example 16, wherein the drive assembly further comprises a guide member, wherein the guide member is in communication with the first and second links, wherein the second link is configured to pivot the guide member, wherein the guide member is configured to pivot a distal portion of the first link.

Example 18

The needle applier cartridge according to Example 17, wherein the guide member comprises at least one protrusion, wherein the protrusion is configured to engage the first link.

Example 19

The needle applier cartridge according to Example 18, wherein the drive assembly further comprises a resilient member, wherein the resilient member is configured to resiliently bear against the guide member.

Example 20

A needle applier cartridge configured to be coupled to a needle applying instrument, the needle applier cartridge comprising: (a) a needle; (b) a drive assembly coupled to the needle, wherein the drive assembly is configured to drive the needle along an orbital path about a rotation axis, wherein the drive assembly comprises a link; and (c) a guide assembly, wherein the guide assembly comprises a guide member, wherein the guide member is pivotably coupled relative to the drive assembly, wherein the guide member is configured to pivot to thereby guide a distal portion of the link along a predetermined path.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body;
   (b) an input feature;
   (c) an elongate shaft extending distally from the body along a longitudinal axis; and
   (d) a needle applier coupled to the elongate shaft, wherein the needle applier comprises:
      (i) a needle,
      (ii) a drive assembly coupled to the needle, wherein the drive assembly comprises a link configured to drive the needle orbitally about a rotation axis that is transverse to the longitudinal axis in response to actuation of the input feature, wherein the link has a first end that is movable along a path that is transverse to the longitudinal axis to thereby rotate the drive assembly about the rotation axis, and
      (iii) a guide assembly, wherein the guide assembly is in communication with the input feature and the the link such that the link is configured to drive movement of the guide assembly, wherein the guide assembly is responsive to the input feature to guide a distal portion of the link along a semi-circular path.

2. The instrument of claim 1, wherein the drive assembly of the needle applier is movable through a drive stroke and a return stroke.

3. The instrument of claim 2, wherein the drive assembly is configured to move through the drive stroke and the return stroke after a single actuation of the input feature.

4. The instrument of claim 2, wherein the drive assembly is configured to move through the drive stroke after a first actuation of the input feature, wherein the drive assembly is configured to move through the return stroke after a second action of the input feature.

5. The instrument of claim 1, wherein the needle applier further comprises a rotary input, wherein the input feature is operable to rotate the rotary input.

6. The instrument of claim 5, wherein the rotary input is in communication with the drive assembly, wherein the rotary input is further in communication with the guide assembly.

7. The instrument of claim 6, wherein the drive assembly is pivotably secured to the rotary input, wherein at least a portion of the guide assembly is slidably secured to the rotary input.

8. The instrument of claim 7, wherein the rotary input comprises a cam feature, wherein the at least a portion of the guide assembly that is slidably secured to the rotary input is configured to slide relative to the cam feature.

9. The instrument of claim 8, wherein the guide assembly is responsive to the cam feature to drive at least a portion of the drive assembly along a semi-circular path.

10. The instrument of claim 1, wherein the needle applier further comprises a linear input, wherein the linear input is in communication with the input feature.

11. The instrument of claim 10, wherein the linear input is in communication with the drive assembly, wherein the linear input is further in communication with the guide assembly.

12. The instrument of claim 11, wherein the linear input is configured to separately drive the drive assembly and the guide assembly in response to a common linear motion provided by the input feature.

13. The instrument of claim 10, wherein the needle applier further comprises a cam plate, wherein the cam plate comprises a cam feature, wherein the drive assembly is configured to engage the cam feature.

14. The instrument of claim 13, wherein the cam feature of the cam plate has a wishbone shape.

15. The instrument of claim 13, wherein the cam feature is configured to translate the drive assembly to drive the needle about the rotation axis.

16. A needle applier cartridge configured to be coupled to a needle applying instrument, the needle applier cartridge comprising:
   (a) a needle; and
   (b) a drive assembly configured to move the needle through an orbital range of motion along a circular path, the drive assembly comprising:
      (i) a first link,
      (ii) a second link, wherein the second link is in communication with the first link, wherein the first link has a longitudinal length greater than the second link, and
      (iii) a needle driver, wherein the needle driver is coupled to at least a portion of the first link, wherein the first link is responsive to the second link to direct the needle driver along a needle drive path.

17. The needle applier cartridge of claim 16, wherein the drive assembly further comprises a guide member, wherein the guide member is in communication with the first and second links, wherein the second link is configured to pivot the guide member, wherein the guide member is configured to pivot a distal portion of the first link.

18. The needle applier cartridge of claim 17, wherein the guide member comprises at least one protrusion, wherein the protrusion is configured to engage the first link.

19. The needle applier cartridge of claim 18, wherein the drive assembly further comprises a resilient member, wherein the resilient member is configured to resiliently bear against the guide member.

20. A needle applier cartridge configured to be coupled to a needle applying instrument, the needle applier cartridge comprising:
   (a) a needle;
   (b) a drive assembly coupled to the needle, wherein the drive assembly is configured to drive the needle along an orbital path about a rotation axis, wherein the drive assembly comprises a link, wherein the link has a proximal end and a distal end and a longitudinal length extending between the proximal end and the distal end, wherein the link is configured to pivot at the proximal end, wherein the link is further configured to pivot at the distal end; and
   (c) a guide assembly, wherein the guide assembly comprises a guide member, wherein the guide member is pivotably coupled relative to the drive assembly, wherein the guide member is configured to pivot to thereby guide a distal portion of the link along a predetermined path.

* * * * *